United States Patent
Tang et al.

(10) Patent No.: US 11,935,627 B2
(45) Date of Patent: Mar. 19, 2024

(54) SYSTEM AND METHOD FOR TEXT-BASED BIOLOGICAL INFORMATION PROCESSING WITH ANALYSIS REFINEMENT

(71) Applicant: AIONCO, Inc., Menlo Park, CA (US)

(72) Inventors: Cheuk Ying Tang, Cupertino, CA (US); Edmund Wong, Mountain View, CA (US); Gene Lee, Millbrae, CA (US)

(73) Assignee: Mujin, Inc., Tokyo (JP)

( * ) Notice: Subject to any disclaimer, the term of this patent is extended or adjusted under 35 U.S.C. 154(b) by 0 days.

(21) Appl. No.: 18/146,901

(22) Filed: Dec. 27, 2022

(65) Prior Publication Data
US 2023/0335223 A1    Oct. 19, 2023

Related U.S. Application Data

(60) Provisional application No. 63/294,802, filed on Dec. 29, 2021.

(51) Int. Cl.
*G16B 20/20* (2019.01)
*G16B 40/20* (2019.01)
*G16B 50/00* (2019.01)

(52) U.S. Cl.
CPC ............ *G16B 40/20* (2019.02); *G16B 20/20* (2019.02); *G16B 50/00* (2019.02)

(58) Field of Classification Search
CPC ......... G16B 40/20; G16B 20/20; G16B 50/00
See application file for complete search history.

(56) References Cited

U.S. PATENT DOCUMENTS

| | | | |
|---|---|---|---|
| 2006/0015264 A1* | 1/2006 | McShea | C12N 15/113 702/20 |
| 2016/0017412 A1* | 1/2016 | Srinivasan | G16B 30/00 506/2 |
| 2016/0019338 A1* | 1/2016 | Chudova | G16B 20/10 702/20 |
| 2016/0210405 A1* | 7/2016 | Rava | C12Q 1/6883 |
| 2016/0306922 A1* | 10/2016 | van Rooyen | G16B 50/30 |
| 2017/0124254 A1* | 5/2017 | van Rooyen | H01L 27/0207 |

(Continued)

FOREIGN PATENT DOCUMENTS

| | | |
|---|---|---|
| CN | 106202968 B | 2/2020 |
| CN | 110011840 B | 4/2021 |
| EP | 3542296 B1 | 4/2021 |

OTHER PUBLICATIONS

PCT International Search Report and Written Opinion dated Apr. 28, 2023 for PCT/US2022/082440 filed Dec. 27, 2022, Applicant: AIONCO, Inc., ISA/KR, 11 pages.

(Continued)

*Primary Examiner* — Eliyah S. Harper
(74) *Attorney, Agent, or Firm* — Perkins Coie LLP

(57) ABSTRACT

Introduced here is an approach to further refining an initial set of target locations that can serve as inputs to machine learning mechanisms. These target locations may refer to unique molecular positions in a reference human genome and/or mutations thereof that are diagnostically relevant for a given cancer type. The system can implement a refinement mechanism to account for unnecessary or problematic data, such as consecutive/overlapping patterns, non-uniform read counts, insufficient data quality, internal processing noises, and/or insufficient data counts.

12 Claims, 10 Drawing Sheets

Specification includes a Sequence Listing.

(56) References Cited

U.S. PATENT DOCUMENTS

| | | | | |
|---|---|---|---|---|
| 2017/0270212 | A1* | 9/2017 | Lavrenko | G16B 20/20 |
| 2017/0270245 | A1* | 9/2017 | van Rooyen | G16B 50/40 |
| 2017/0322217 | A1* | 11/2017 | Batagov | G16B 20/10 |
| 2017/0362638 | A1* | 12/2017 | Chudova | G16B 30/10 |
| 2018/0201991 | A1* | 7/2018 | Zhang | C12Q 1/6886 |
| 2019/0211393 | A1* | 7/2019 | Rabinowitz | C12Q 1/6883 |
| 2020/0202975 | A1* | 6/2020 | Lee | G16B 20/20 |
| 2020/0342956 | A1* | 10/2020 | Schwartz | G16B 40/00 |
| 2022/0199196 | A1* | 6/2022 | Korbel | G16B 30/00 |
| 2022/0254442 | A1* | 8/2022 | Dolzhenko | G16B 20/10 |
| 2023/0056396 | A1* | 2/2023 | Mourao | G16B 40/20 |
| 2023/0122305 | A1* | 4/2023 | Senapathy | C12Q 1/6883 |
| | | | | 435/6.11 |

OTHER PUBLICATIONS

Khorshed, Tarek et al., "Deep Learning for Multi-Tissue Cancer Classification of Gene Expressions (GeneXNet)," May 6, 2020, IEEEAccess vol. 8, 2020, pp. 90615-90629.

Barton, Alison R., "Whole-exome imputation within UK Biobank powers rare coding variant association and fine-mapping analyses," Nature Genetics Analysis, vol. 53, Aug. 2021, 15 pages.

Homomorphic Encryption References, Homomorphic Encryption Standardization Webpage, last accessed Jul. 31, 2021, http://people.csail.mit.edu/vinodv/FHE/FHE-refs.html , 5 pages.

* cited by examiner

SEQUENCE LISTING

```
Sequence total quantity: 19
SEQ ID NO: 1            moltype = DNA   length = 34
FEATURE                 Location/Qualifiers
source                  1..34
                        mol_type = genomic DNA
                        organism = Homo sapiens
SEQUENCE: 1
ttggataacc tagaaaaaaa acaaattact ggaa                                  34

SEQ ID NO: 2            moltype = DNA   length = 30
FEATURE                 Location/Qualifiers
source                  1..30
                        mol_type = genomic DNA
                        organism = Homo sapiens
SEQUENCE: 2
ggataaccta gaaaaaaaaa aacaaattac                                       30

SEQ ID NO: 3            moltype = DNA   length = 30
FEATURE                 Location/Qualifiers
source                  1..30
                        mol_type = genomic DNA
                        organism = Homo sapiens
SEQUENCE: 3
ggataaccta gaaaaaaaaa acaaattact                                       30

SEQ ID NO: 4            moltype = DNA   length = 30
FEATURE                 Location/Qualifiers
source                  1..30
                        mol_type = genomic DNA
                        organism = Homo sapiens
SEQUENCE: 4
ggataaccta gaaaaaaaaa caaattactg                                       30

SEQ ID NO: 5            moltype = DNA   length = 30
FEATURE                 Location/Qualifiers
source                  1..30
                        mol_type = genomic DNA
                        organism = Homo sapiens
SEQUENCE: 5
ggataaccta gaaaaaaaac aaattactgg                                       30

SEQ ID NO: 6            moltype = DNA   length = 30
FEATURE                 Location/Qualifiers
source                  1..30
                        mol_type = genomic DNA
                        organism = Homo sapiens
SEQUENCE: 6
ggataaccta gaaaaaaaca aattactgga                                       30
```

```
SEQ ID NO: 7            moltype = DNA  length = 30
FEATURE                 Location/Qualifiers
source                  1..30
                        mol_type = genomic DNA
                        organism = Homo sapiens
SEQUENCE: 7
ggataaccta gaaaaaacaa attactggaa                                    30

SEQ ID NO: 8            moltype = DNA  length = 30
FEATURE                 Location/Qualifiers
source                  1..30
                        mol_type = genomic DNA
                        organism = Homo sapiens
SEQUENCE: 8
ggataaccta gaaaaacaaa ttactggaaa                                    30

SEQ ID NO: 9            moltype = DNA  length = 17
FEATURE                 Location/Qualifiers
source                  1..17
                        mol_type = genomic DNA
                        organism = Homo sapiens
SEQUENCE: 9
atcatcatca tcatcat                                                  17

SEQ ID NO: 10           moltype = DNA  length = 24
FEATURE                 Location/Qualifiers
source                  1..24
                        mol_type = other DNA
                        organism = synthetic construct
variation               4..19
SEQUENCE: 10
acttgaatca tcatcatcct ccta                                          24

SEQ ID NO: 11           moltype = DNA  length = 24
FEATURE                 Location/Qualifiers
source                  1..24
                        mol_type = other DNA
                        organism = synthetic construct
variation               5..20
SEQUENCE: 11
acttgaatca tcatcatcct ccta                                          24

SEQ ID NO: 12           moltype = DNA  length = 24
FEATURE                 Location/Qualifiers
source                  1..24
                        mol_type = other DNA
                        organism = synthetic construct
S_region                6..21
SEQUENCE: 12
acttgaatca tcatcatcct ccta                                          24

SEQ ID NO: 13           moltype =     length =
SEQUENCE: 13
000

SEQ ID NO: 14           moltype =     length =
SEQUENCE: 14
000

SEQ ID NO: 15           moltype =     length =
SEQUENCE: 15
000

SEQ ID NO: 16           moltype =     length =
SEQUENCE: 16
000

SEQ ID NO: 17           moltype =     length =
SEQUENCE: 17
000

SEQ ID NO: 18           moltype = DNA  length = 13
FEATURE                 Location/Qualifiers
source                  1..13
                        mol_type = genomic DNA
                        organism = Homo sapiens
SEQUENCE: 18
ttggataacc tag                                                      13
```

```
SEQ ID NO: 19         moltype = DNA   length = 23
FEATURE               Location/Qualifiers
source                1..23
                      mol_type = other DNA
                      organism = synthetic construct
SEQUENCE: 19
nnnatcatca tcatcatcat nnn                                              23
```

SYSTEM AND METHOD FOR TEXT-BASED BIOLOGICAL INFORMATION PROCESSING WITH ANALYSIS REFINEMENT

CROSS-REFERENCE TO RELATED APPLICATION(S)

The present application claims the benefit of U.S. Provisional Patent Application No. 63/294,802 filed Dec. 29, 2021, the entirety of which is incorporated herein by reference.

REFERENCE TO SEQUENCE LISTING

This application contains an ST.26 compliant Sequence Listing, which is submitted concurrently in xml format via EFS-Web or Patent Center and is hereby incorporated by reference in its entirety. The .xml copy, created on Jun. 27, 2023, is named 145289.8004.US01 Sequence Listing.xml and is 14.5 KB in size.

TECHNICAL FIELD

Various implementations concern computer programs and associated computer-implemented techniques for processing sequenced information, such as text-based representation of genetic information.

BACKGROUND

Genes are pieces of deoxyribonucleic acid (DNA) inside cells that indicate how to make the proteins that the human body needs to function. At a high level, DNA serves as the genetic "blueprint" that governs operation of each cell. Genes can not only affect inherited traits that are passed from a parent to a child, but can also affect whether a person is likely to develop diseases like cancer. Changes in genes—also called "mutations"—can play an important role in the physiological conditions of the human body, such as in the development of cancer. Accordingly, genetic testing may be leveraged to detect such physiological conditions or likely onsets thereof.

The term "genetic testing" may be used to refer to the process by which the genes or portions of genes of a person are examined to identify mutations. There are many types of genetic tests, and new genetic tests are being developed at a rapid pace. While genetic testing can be employed in various contexts, it may be used to detect mutations that are known to be associated with cancer.

Genetic testing could also be employed as a means for addressing or treating the physiological condition. For example, after a person has been diagnosed with cancer, a healthcare professional may examine a sample of cells to look for changes in the genes in tracking the progress of the cancer, the treatment, etc. These changes may be indicative of the health of the person (and, more specifically, progression/regression of the cancer). Insights derived through genetic testing may provide information on the prognosis, for example, by indicating whether treatment has been helpful in addressing the mutation.

Implementing computing technologies for the genetic testing may yield valuable insights. For example, artificial intelligence and machine-learning technologies may be leveraged to analyze DNA information for detecting and/or addressing cancers or potential onset of cancers. However, the magnitude of the DNA information, the large number of potential mutations, large number of samples, and other similar factors often negatively impact the effectiveness, the accuracy, and the practicality in leveraging such computing technologies for the genetic testing.

Figure 1A:
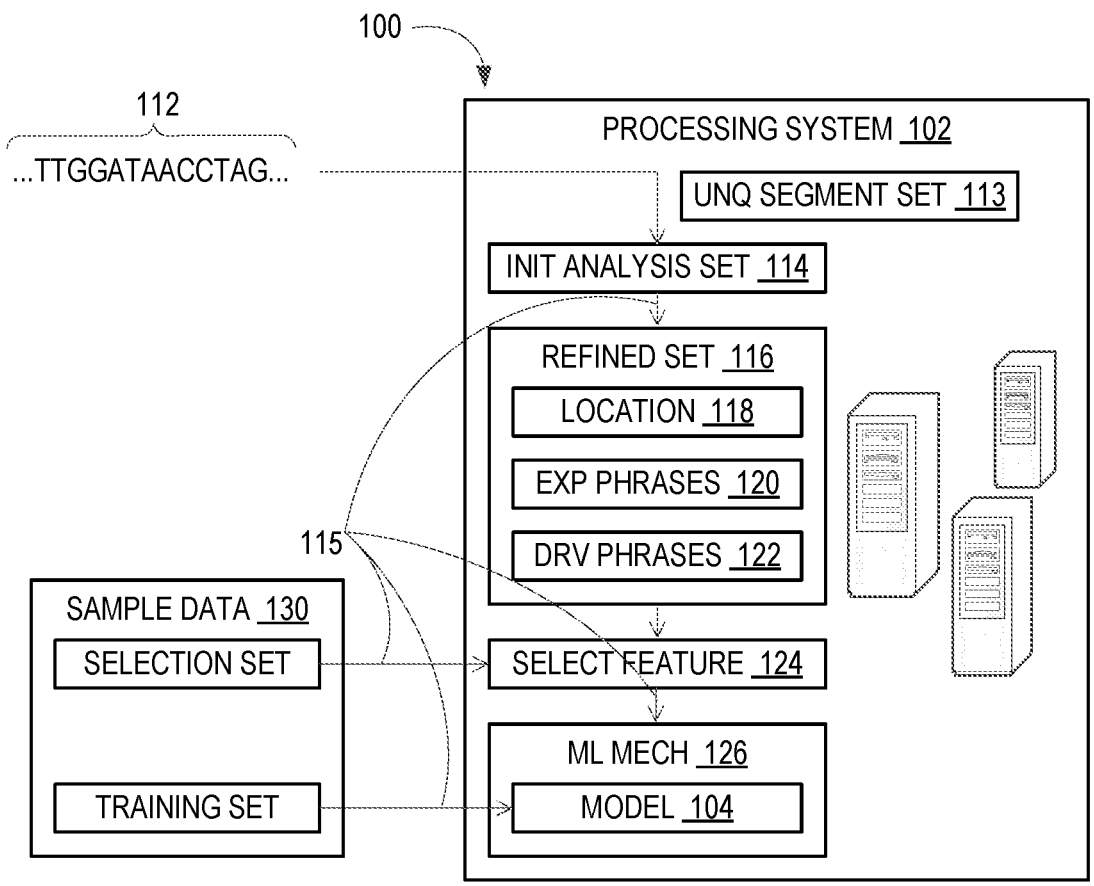
FIG. 1A (SEQ ID NO: 18) and 1B show example operating environments of a computing system including a genetic information processing system in accordance with one or more implementations of the present technology.

Various features of the technology described herein will become more apparent to those skilled in the art from a study of the Detailed Description in conjunction with the drawings. Various implementations are depicted in the drawings for the purpose of illustration. However, those skilled in the art will recognize that alternative implementations may be employed without departing from the principles of the technology. Accordingly, although specific implementations are shown in the drawings, the technology is amenable to various modifications.

DETAILED DESCRIPTION

Genetic testing may be beneficial for diagnosing and treating cancer. For example, identifying mutations that are indicative of cancer can help (1) healthcare professionals make appropriate decisions, (2) researchers to direct their investigations, and (3) precision medicine to design better therapies. However, discovering these mutations tends to be difficult, especially as the number of cancers of interest (and thus, corresponding data) increases.

While computer-aided detection (CADe) and computer-aided diagnostic (CADx) processing systems may be used to analyze the genetic testing data, conventional approaches still face several drawbacks due to the overwhelming number of computations required for such analysis. For example, conventional systems may identify a number of molecular positions (e.g., target analysis locations) and combinations that may be inefficient, ineffective, inaccurate, or otherwise impractical to process. Moreover, such deficiencies become even more problematic when the system is tasked with reviewing the genetic information of tens, hundreds, or thousands of patients. In other words, even if a conventional system is able to comprehensively analyze the genetic information of a single patient, reviewing the genetic information of tens, hundreds, or thousands of patients during actual deployment becomes impractical due to the processing delays and inaccuracies.

Introduced here is an approach that can be implemented by a computing system to predict and/or diagnose in an improved manner. Implementations of the present technology can include the computing system processing the genetic information as relatively simple/smaller computer-readable data, such as text strings (simpler/smaller in comparison to, e.g., image data). Using the textual representations, the computing system can identify specific text patterns, such as unique segments of repeated characters (e.g., tandem repeats (TRs) corresponding to sequences of two or more DNA bases that are repeated numerous times in a head-to-tail manner on a chromosome), phrases surrounding the unique segments, and derivations/mutations thereof, used to analyze nucleic acid sequences (or simply "sequences"). In some implementations, the computing system can focus on the unique phrases and/or derivations thereof in characterizing and/or recognizing one or more types of cancer. In some implementations, the computation system can select features from the phrases/derivations and may ignore other portions of the overall text string or sequence, thereby reducing the overall computations in developing, training, and/or applying a machine learning (ML) model or other artificial intelligence mechanisms. While implementation of the approach may result in improvements across different aspects of mutation discovery, there are several notable improvements worth mentioning.

Advantageously, the approach allows models to be trained (and diagnoses to be predicted by those trained models) in a more time- and resource-efficient manner as the number of features considered by the computing system may be reduced (e.g., from tens of thousands of nucleotide locations to several thousand nucleotide locations). For a given type of cancer, the computing system can reduce an expanded feature set that is discovered through examination of training of genetic information through ML, so as to identify the most important nucleotide locations from a diagnostic perspective without significantly harming the accuracy in identifying mutations that are indicative of the given cancer type.

In some implementations, the computing system can include and/or utilize a mutation analysis mechanism that identifies a set of unique portions or segments in the human genome/DNA and related mutations that correspond to development/onset of certain types of cancer. The computing system can identify the set of unique portions or phrases and mutations (e.g., text strings having a length of k) based on the TRs. The computing system may use a refinement mechanism to further process or filter the set of unique portions and mutations. For example, the computing system can use the refinement mechanism to remove duplicate entries, overlapping entries, comparison-based errors, unqualified data, physiology-based noise parameters, and/or the like within the set. Through the additional refinement, the computing system can further reduce the total number of computations required to analyze and process the genetic information (e.g., in developing and/or implementing the ML model). Moreover, the refinement mechanism can provide reduced errors caused by duplicate computations, excessive computations, insufficient/inconsistent sample sizes, poor data quality, and the like.

Implementations may be described in the context of instructions that are executable by a system for the purpose of illustration. However, those skilled in the art will recognize that aspects of the technology described herein could be implemented via hardware, firmware, or software. As an example, a computer program that is representative of a software-implemented genetic information processing platform (or simply "processing platform") designed to process genetic information may be executed by the processor of a system. This computer program may interface, directly or indirectly, with hardware, firmware, or other software implemented on the system. Moreover, this computer program may interface, directly or indirectly, with computing devices that are communicatively connected to the system. One example of a computing device is a network-accessible storage medium that is managed by a healthcare entity (e.g., a hospital system or diagnostic testing facility).

Overview of Genetic Information Processing System

Figure 1B:
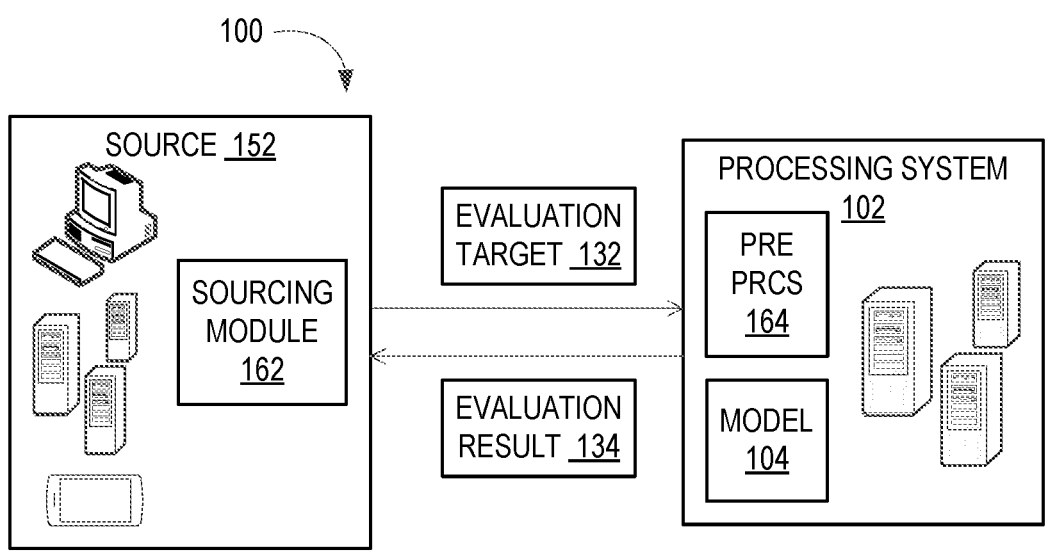

FIGS. 1A and 1B show example operating environments of a computing system 100 including a genetic information processing system 102 ("processing system 102") in accordance with one or more implementations of the present technology. The processing system 102 can include one or more computing devices, such as servers, personal devices, enterprise computing systems, distributed computing systems, cloud computing systems, or the like. The processing system 102 can be configured to analyze DNA information for diagnosing one or more types of cancer, for evaluating development stages leading up to the onset of the one or more types of cancer, and/or for predicting a likely onset of the one or more types of cancer.

The application environment depicted in FIG. 1A can represent a development or training environment in which the processing system 102 develops and trains an analysis mechanism, such as a ML model 104, configured to detect a presence, a progress, and/or a likely onset of one or more types of cancer. In developing and training the ML model 104, the processing system 102 can first identify an analysis template (e.g., specific data locations or values within a reference data 112, such as the human genome or other data derived from human/patient DNA) targeted for further analysis/consideration.

As an illustrative example, the processing system 102 can use a text-based representation (e.g., one or more text strings) of the human DNA as the reference data 112. The processing system 102 can analyze the reference data 112 to identify specific locations and/or corresponding text sequences that can be utilized as identifiers or comparison points in subsequent processing. In some implementations, the processing system 102 can use a set of unique text segments 113 (e.g., a set of unique TRs) found or expected in the reference data 112 to generate an initial analysis set 114. The processing system 102 can generate the initial analysis set 114 by identifying expected phrases 120 that include the unique segment set 113 and/or by computing derivations thereof (e.g., derived phrases 122) that represent mutations targeted for analysis. The initial analysis set 114 and/or the unique segment set 113 can include location identifiers 118 associated with a relative location of such segments, phrases, and/or derivations within the reference data 112.

The processing system 102 can further use a refinement mechanism 115 (e.g., a software routine or a set of instructions) that further operates on the initial analysis set 114 and/or subsequent data processing. The refinement mechanism 115 can filter result of one or more data processing leading up to the design and/or training of the ML model.

The refinement mechanism 115 can generate the filtered result of the initial analysis set 114 as the refined set 116. Additionally or alternatively, the refinement mechanism 115 may be configured to filter during or after the feature selection process and/or the sample data 130.

In some implementations, the refinement mechanism 115 can process the unique segment set 113 and/or the initial analysis set 114 to generate a refined set 116. For example, the refinement mechanism can be configured to remove (1) overlapping TRs from the set of unique segment set 113, (2) remove duplicated phrases from the initial analysis set 114, (3) filter or adjust for sample data 130 (e.g., text-based DNA data representative of healthy individuals, cancerous tissues, and/or non-cancerous tissues collected from cancer patients) used to develop/train the ML model 104, and/or (4) adjust for or filter physiological or processing noises. Details regarding the derivation of the initial template and the refinement thereof are described below.

For the feature selection, the processing system 102 can iteratively add or remove one or more unique locations/sequences and/or derivations from the refined set 116 and calculate a correlation or an effect of the removed data point on the duplicating the known classifications of the sample data 130 (e.g., to accurately recognize the different categories of the sample data 130). The processing system 102 can determine a set of selected features 124 that correspond to the unique locations/phrases and derivations thereof having at least a threshold amount of affect or correlation with one or more corresponding cancer types. In other words, the processing system 102 can determine the set of features 124 including locations, sequences, mutations or combinations thereof that are deterministic/characteristic of or commonly occurring in corresponding cancers. Based on the selected set of features 124, the processing system 102 can implement a ML mechanism 126 (e.g., random forest, neural network, etc.) to generate the ML model 104. The processing system 102 can further train the ML model 104 using training data.

Using the filtered/refined results, the processing system 102 can limit the amount of data considered or processed in subsequent analyses, such as in feature selection, model generation, model training, and/or the like. For example, the processing system 102 can use the refinement mechanism 115 to reduce the size of the unique segment set 113, thereby reducing the expected phrases 120 and the derived phrases 122 that correspond to the unique segment set 113. Also, the processing system 102 can use the refinement mechanism 115 to further reduce the size of the initial analysis set 114, such as by removing potential duplicated phrases (e.g., across expected/derived phrases at different locations). Accordingly, the processing system 102 can reduce the resource consumption through the reduced size of the refined set 116 (e.g., in comparison to the initial analysis set 114) and reduce the noises and other negative impacts generated by the overlapping/duplicative phrases. Additional sample-based, process-based, and/or physiology-based refinement can further increase the overall performance and accuracy of the resulting ML model 104.

The application environment depicted in FIG. 1B can represent a deployment environment in which the processing system 102 applies the analysis mechanism to detect a presence, a progress, and/or a likely onset of one or more types of cancer from evaluation target 132 (e.g., text-based form of patient DNA data). The processing system 102 can generate an evaluation result 134 based on testing the evaluation target 132 with the ML model 104. The processing system 102 can generate the evaluation result 134 that represents a cancer diagnosis or a cancer signature/signal. For example, the evaluation result 134 can represent a determination that the patient has cancer, a stage (e.g., clinically recognized stages 1-4) of the onset cancer, a progress state before/leading up to an onset state of cancer, a likelihood of developing cancer within a predetermined period, an identification of the type of cancer, or a combination thereof.

As an illustrative example, the computing system 100 can include a sourcing device 152 that provides the evaluation target 132 and/or receives the evaluation result 134. The sourcing device 152 can be operated by a patient submitting the evaluation target 132, a healthcare service provider associated with the patient, an insurance company, or the like. Some examples of the sourcing device 152 can include a personal device (e.g., a personal computer, a mobile computing device, such as a smart phone or a tablet, or the like), a workstation, an enterprise device, etc.

In some implementations, the computing system 100 can include a sourcing module 162 operating on the source device 152. The sourcing module 162 can include a device/circuit and/or a software module (e.g., a codec, an app, or the like) that generates or pre-processes the evaluation target 132. For example, the sourcing module 162 can include a homomorphic encoder that encrypts and prevents unauthorized access to the patient data. The evaluation target 132 can include the homomorphically encoded data that can be processed at the processing system 102 without fully decrypting and recovering the patient data. In other words, the processing system 102 can apply the ML model 104 that is configured to process or perform computations on the encrypted data.

The processing system 102 can include a pre-processing module 164 that conditions the evaluation target 132 for and/or during the model application. For example, the pre-processing module 164 can include circuits and/or software instructions that are configured to remove biases or noises introduced before receiving the evaluation target 132 and/or during the processing (e.g., bootstrapping module to remove noise/uncertainties introduced by processing encrypted data) of the evaluation target 132.

Data Processing Formats

Figure 2:
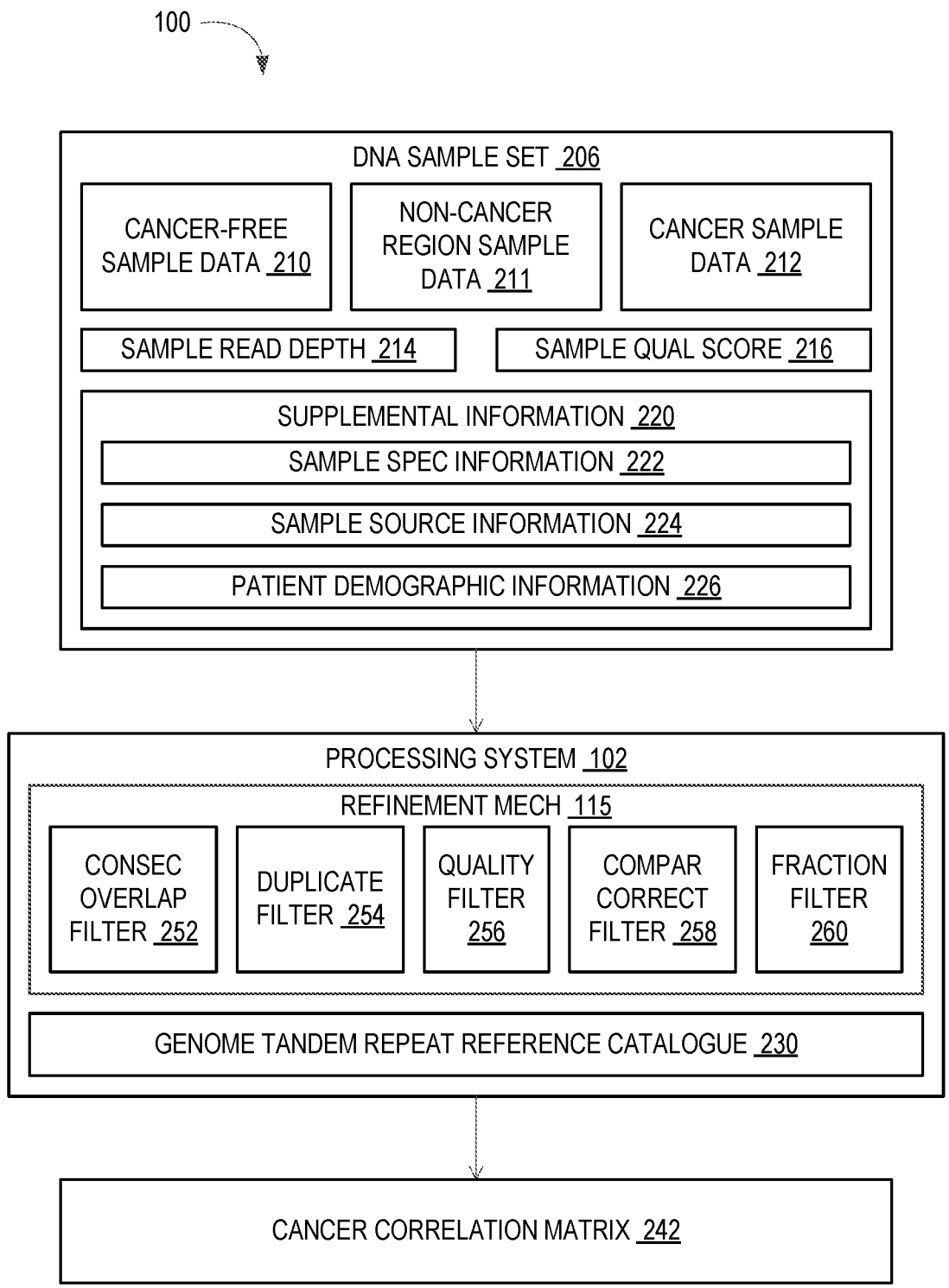
FIG. 2 shows an example data processing format for the genetic information processing system in accordance with one or more implementations of the present technology.

In developing/training the model 104 and/or deploying the model 104, the computing system 100 can utilize a variety of data processing formats (e.g., data structures, organizations, inputs/outputs, or the like). FIG. 2 shows an example data processing format for the processing system 102 in accordance with one or more implementations of the present technology. The processing system 102 can receive and process a DNA sample set 206 (e.g., an instance of the reference data 112 and/or sample data 130 illustrated in FIG. 1A) having one or more of the formats or subfields illustrated in FIG. 2. Moreover, the processing system 102 can generate the initial analysis set 114 (FIG. 1A) and the refined set 116 (FIG. 1A) using one or more detailed example aspects depicted in FIG. 2.

As an illustrative example, the DNA sample set 206 can include DNA data (e.g., representative of a set of sequenced DNA information) corresponding to different known categories. Examples of the DNA sample set 206 can include genetic information (e.g., text-based representations) derived or extracted from human bodies, such as from tissue extracted during a biopsy or from cell-free DNA (e.g., DNA that is not encapsulated within a cell) in bodily fluids. The DNA sample set 206 can include DNA data collected from volunteers or participating patients having medically confirmed diagnoses and/or from public or private databases.

The DNA sample set 206 can include data collected from different types/categories of samples, such as cancer-free samples (cancer-free data 210), non-cancerous regions/samples (non-regional data 211), and/or cancerous samples (cancer-specific data 212). The cancer-free data 210 can represent text-based DNA data corresponding to samples collected from patients confirmed/diagnosed to be cancer free. The non-regional data 211 can represent text-based DNA data corresponding to samples collected from non-cancerous regions (e.g., white blood cells or leukocytes) of patients confirmed/diagnosed to have one or more types of cancer. The cancer-specific data 212 can represent text-based DNA data corresponding to samples (e.g., tumor biopsies, liquid biopsies, etc.) collected from cancerous regions or tumors confirmed/diagnosed to be a specified type of cancer. The DNA sample set 206 can include information (e.g., the non-regional data 211 and/or the cancer-specific data 212) corresponding to one or more types of cancers (e.g., breast cancer, lung cancer, colon cancer, and/or the like).

The DNA sample set 206 can further include descriptions regarding a strength or a trustworthiness of the data. For example, the DNA sample set 206 can include a sample read depth 214 and/or a sample quality score 216. The sample read depth 214 can represent a number of times a given nucleotide in the genome (e.g., certain text string/portion) was detected in a sample. The sample read depth 214 may correspond to a sequencing depth associated with processing fragmented sections of the genome within a tissue sample. The sample quality score 216 can represent a quality of identification of the nucleobases generated by DNA sequencing. In some implementations, the sample quality score 216 can include a phred quality score.

The DNA sample set 206 can also include supplemental information 220 that describes other aspects of the sample or the source of the data. For example, the supplemental information 120 can include information such as sample specification information 122 (or simply "specification information"), sample source information 124 (or simply "source information"), patient demographic information 126, or a combination thereof.

The specification information 122 can include technical information or specifications about the sequenced DNA associated with the DNA sample set 206. For example, the specification information 122 can include information about the locations 118 (FIG. 1A) within the genome to which the DNA fragments correspond, such as intron and exon regions, specific genes, or chromosomes. Also, the specification information 122 can describe, e.g., (1) the process, methods, and instrumentation used to extract and sequence the genetic material, (2) the number of sequencing reads for each sample, or a combination thereof.

The source information 124 can include details regarding the source and/or the categorization of the sample. For example, the source information 124 can include information about the cancer type, the stage of cancer development, the organ or tissue from which the sample was extracted, or a combination thereof.

The patient demographic information 126 can include demographic details of the patient from which the sample was taken. For example, the patient demographic information 126 can include the age, the gender, the ethnicity, the geographic location of where the patient resides/visited, the duration of residence/visitation, predispositions for genetic disorders or cancer development, family history, or a combination thereof.

The processing system 102 can analyze the DNA sample set 206 using the mutation analysis mechanism. Accordingly, the processing system 102 can identify mutations or mutation patterns in specific DNA sequences that can be used as markers to determine the existence, the progress, and/or the developing stages of a particular form of cancer. To identify the relevant mutations, the processing system 102 can detect a set of targeted locations or text patterns (according to, e.g., the TRs) within the reference genomes.

The processing system 102 can generate and/or utilize a genome tandem repeat reference catalogue 230 that represents a catalogue or a collection of uniquely identifiable TRs in the human genome. As an example, the genome tandem repeat reference catalogue 230 can be based on a reference human genome (e.g., the reference data 112), such as the GRCh38 reference genome. The uniquely identifiable sequences can include DNA sequences having therein a series of multiple instances of directly adjacent identical repeating nucleotide units or base patterns, such as microsatellite DNA sequences. The base patterns can have a predetermined length, such as one for a repetition of one letter or monomer (e.g., 'AAAA') or greater (e.g., three for tetramers, such as 'ACT'). Such uniquely identifiable TRs can serve as reference sequences (e.g., reference locations within the human genome) or markers for evaluating the DNA sample set 206. Since the DNA sample set 206 may correspond to incomplete DNA fragments, the unique TRs found within the fragments may be used to map the DNA information to the human genome.

The processing system 102 can use the genome tandem repeat reference catalogue 230 to compute the initial analysis set 114. For example, the processing system 102 can use the unique TRs identified in the genome tandem repeat reference catalogue 230 to generate derived strings that represent potential mutations. In some implementations, the processing system 102 can identify text characters preceding and/or following each unique TR and derive the mutation strings that represent one or more types of mutations (e.g., insertion-deletion (indel) mutations). Details regarding the initial analysis set 114 (e.g., strings with flanking characters and/or mutation strings) are described below.

The processing system 102 can compare the mutations at the targeted locations/patterns across the different types of DNA sample set 206. Based on the comparison, the processing system 102 can compute a correlation between or a likely contribution of the mutations at the targeted locations/sequences and the development of cancer. Accordingly, the processing system 102 may generate a cancer correlation matrix 242 that correlates identified tumorous sequences or text-based patterns to specific types of cancer. For example, the cancer correlation matrix 242 can be an index that includes multiple instances of the uniquely identifiable tandem repeat sequences in the genome TR reference catalogue 230 that, when found to be tumorous, indicate the existence of a particular form of cancer or indicate the possibility that a particular form of cancer will develop.

The processing system 102 can perform the feature selection using the cancer correlation matrix 242, such as by retaining the locations/patterns and/or derived mutation patterns having at least a predetermined degree of correlation to one or more corresponding types of cancer. Using the selected features, the processing system 102 can develop and train the ML model 104 configured to detect, predict, and/or evaluate development or onset of cancer.

In some implementations, the processing system 102 can further use the refinement mechanism 115 to generate the refined set 116 (FIG. 1A). The refinement mechanism 115 may include one or more filters to enhance the genome TR reference catalogue 230, the initial analysis set 114, and/or corresponding features, such as by removing or adjusting one or more erroneous or unnecessary sequences. For example, the refinement mechanism 115. For example, the refinement mechanism 115 can include: (1) a consecutive overlap filter 252 configured to remove consecutive or overlapping sequences (e.g., unique TRs) that effectively point to the same location, (2) a duplicate filter 254 configured to remove duplicate sequences, such as between mutation strings at different locations, (3) a quality filter 256 configured to remove/adjust for input sample data, such as based on quality and/or input depth, (4) a comparison correction filter 258 configured to remove computational noise or errors, (5) a physiology-based filter, such as a fraction filter 260, configured to remove or adjust for physiological and/or collection-based features that interfere with the data processing, or a combination thereof. Details regarding the refinement mechanism 115 is described below.

Base Text Patterns—Segments

Figures 3A, 3B:
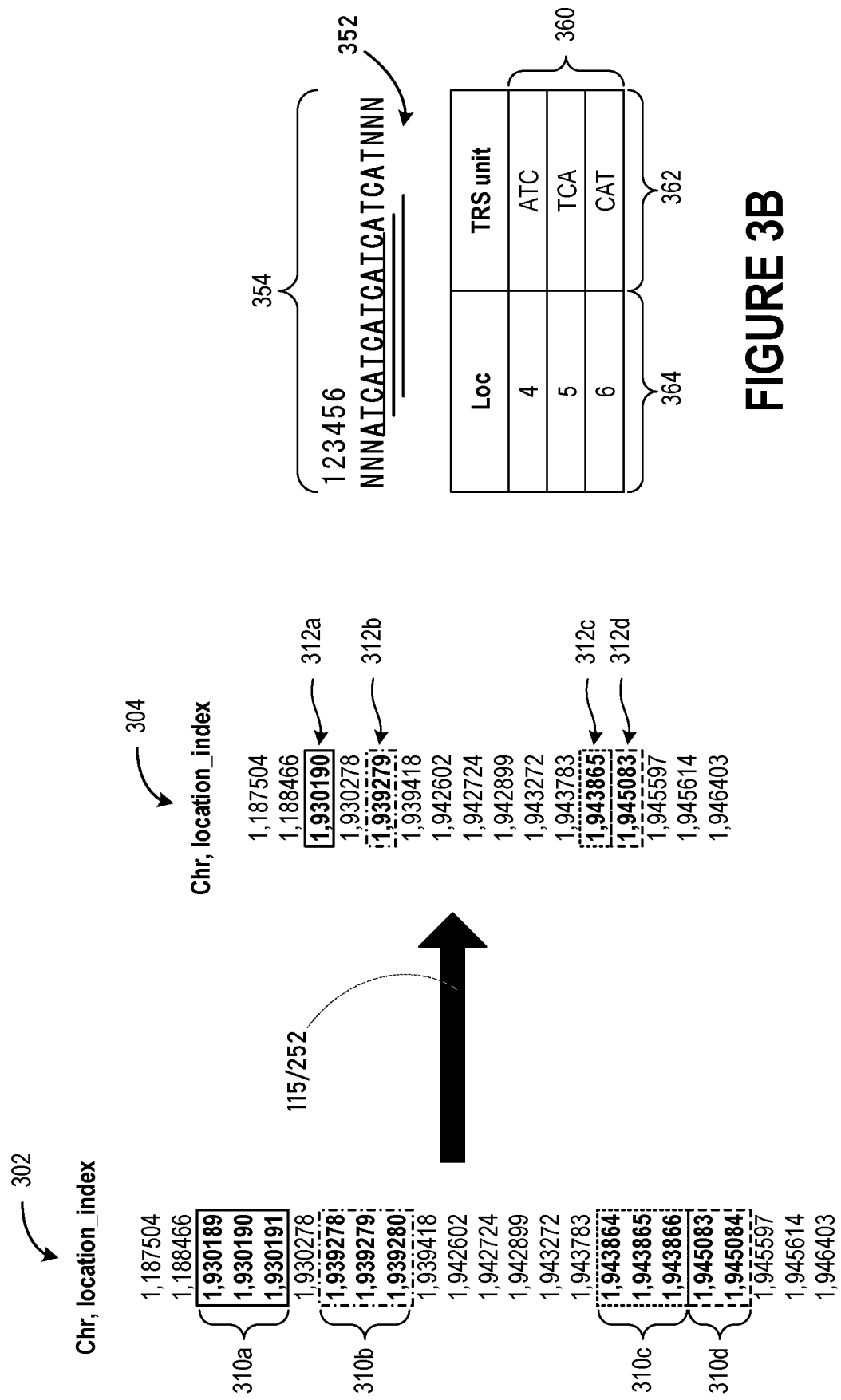
FIGS. 3A and 3B (SEQ ID NO: 19) show examples of unique segments and refinements thereof in accordance with one or more implementations of the present technology.

For describing further detailed aspects of the data format, FIGS. 3A and 3B show examples of unique segments (e.g., uniquely identifiable TRs within the human genome) and refinements thereof in accordance with one or more implementations of the present technology. FIG. 3A shows an initial segment set 302 and a refined segment set 304 that correspond to the unique segments 113 of FIG. 1. FIG. 3B illustrates example overlaps 352 in the initial segment set 302. Referring to FIGS. 3A and 3B together, the processing system 102 can use the refinement mechanism 115 (e.g., the consecutive overlap filter 252) to remove the overlaps 352 therein and generate the refined segment set 304.

In some implementations, the processing system 102 can generate the initial segment set 302 based on analyzing the reference data 112 (FIG. 1A) to find uniquely identifiable patterns. For example, the processing system 102 can generate the initial segment set 302 by identifying uniquely identifiable TRs within the human genome. The processing system 102 can use base or TR units (e.g., base character patterns having controllable lengths of one or more characters that are repeated) to identify the overall TR or segment having a corresponding length (e.g., two or more multiples of the TR unit length). The processing system 102 can generate the initial segment set 302 based on including repeated patterns of the TRs exceeds a minimum number of base pairs. For example, the repeated TR sequence can be selected based on using the repeated base unit having the minimum number of base pairs ranging between five and eight base pairs.

In the initial segment set 302, the processing system 102 may end up including the overlaps 352 that effectively correspond to a longer and unique string segment and the corresponding location. For the example illustrated in FIG. 3B, a target sequence 354 (e.g., a sequence/combination of nucleotides, such as a portion of the DNA information) can include a uniquely identifiable segment ('ATCATCATCAT-CATCAT' (SEQ ID NO: 9) having 17 characters). The processing system 102 can identify unique segments 360 within the target sequence 354 based on identifying repeated adjacent patterns of base units 362. The length of the repeated base units 362 and/or the number of repeats may be predetermined or adjusted in generating the initial segment set 302. For the illustrated example, the targeted segment length corresponds to 12 characters or four repeats of three-letter TR units. Along with the repeated base units 362, the unique segments 360 can be identified based on corresponding segment locations 364 that identify positions (e.g., first letter positions) of the segments within the target sequence 354.

When the target sequence 354 includes a repeated pattern that exceeds the targeted segment length, one target sequence 354 can be identified as including repeats of multiple instances of the base units 356 (e.g., 'ATC,' 'TCA,' and 'CAT'). The multiple instances of the base units 356 may correspond to shifted results of each other. As such, the multiple unique segments 360 can overlap each other and/or be sequentially shifted by one or more characters relative to each other. FIG. 7A illustrates a portion of the initial segment set 302 having overlapping location sets 310a, 310b, 310c, and 310d that correspond to such overlapping instances of the unique segments 360. However, given the nature of the overlaps, each of the overlapping location sets 310a, 310b, 310c, and 310d can effectively correspond to a single segment/location rather than the multiple separate segments/locations.

The processing system 102 can use the refinement mechanism 115 to identify and remove the overlaps 352 in the unique segments 360. In some implementations, the consecutive overlap filter 252 can be configured to ensure that the initial segment set 302 is sorted according to the segment location 358. With the sorted segments, the consecutive overlap filter 252 identify patterns in the segment location 358 of adjacent segments within the initial segment set 302. The consecutive overlap filter 252 can be configured to identify the overlaps 352 when the segment location 358 of the adjacent segments are separated by a predetermined number (e.g., one, two, or more, a number based on the repeated unit length and/or the targeted segment length, and/or the like). Also, the consecutive overlap filter 252 can be configured to identify the overlaps 352 when the segment location 358 follows one or more pattern (e.g., consistently separated by one or two values) over two, three, or more adjacently occurring segments. The consecutive overlap filter 252 can group the two or more adjacent segments that satisfy the separation threshold/pattern as a set of the overlaps.

Additionally or alternatively, the consecutive overlap filter 252 can configured to identify the overlaps 352 when the repeated base units 356 for the adjacent segments correspond to circularly shifted values. For the example illustrated in FIG. 3B, the processing system 102 can identify that the unique segments 360 at locations 4, 5, and 6 correspond to an overlapping set since the repeated base units 356 of 'ATC,' 'TCA,' and 'CAT' correspond to circularly shifting a preceding unit by one character/position. The consecutive overlap filter 252 can group the two or more adjacent segments that satisfy/maintain the detected pattern in the repeated base units 356 a set of the overlaps.

Once the sets of overlaps are identified, the consecutive overlap filter 252 can refine the set by reducing the number of overlapped segments. For example, the consecutive overlap filter 252 can retain one segment from each set of overlaps and remove others. In some implementations, the consecutive overlap filter 252 can be configured to select the segment according to a predetermined location, the target segment length, the repeated unit length, or a combination thereof. For example, the consecutive overlap filter 252 can be configured to select the segment positioned in the middle/center of the set. Also, the consecutive overlap filter 252 can include a predetermined equation that identifies the selection location according to the number of segments in the set, the target segment length, the repeated unit length, or a combination thereof. The selected locations can be represented as refined locations (e.g., refined locations 312a, 312b, 312c, and 312d respectively corresponding to overlapping sets 310a, 310b, 310c, and 312d) in the refined segment set 304.

Base Text Patterns—Expected Phrases

Figure 4:
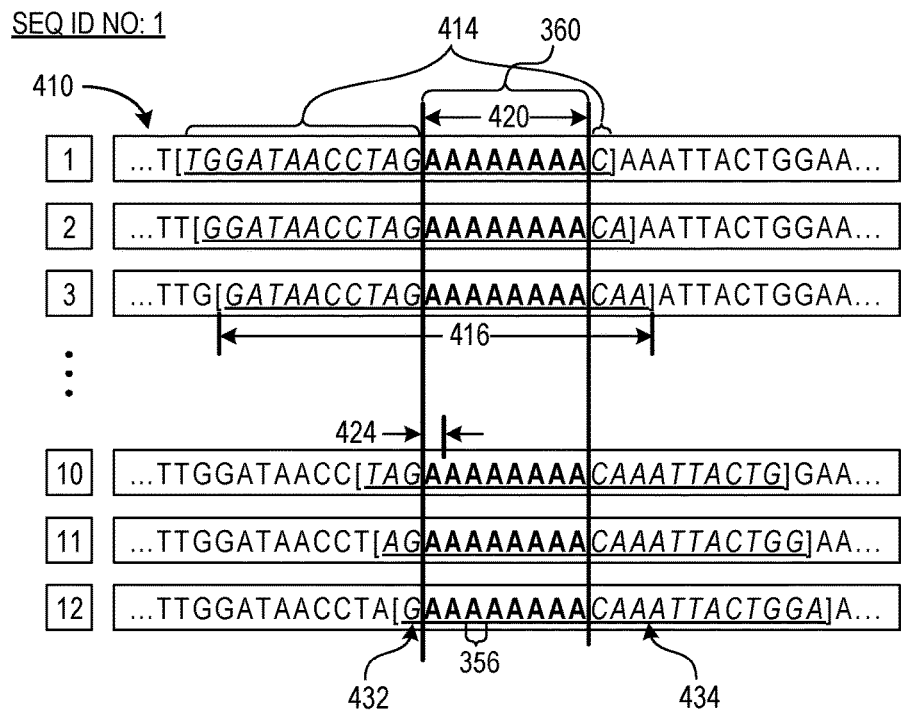
FIG. 4 shows example expected phrases in accordance with one or more implementations of the present technology.

The processing system 102 can use the processed segments (e.g., the refined segment set 304) to generate phrases. FIG. 4 shows example expected phrases 410 in accordance with one or more implementations of the present technology. The expected phrases 410 can correspond to textual representations of the DNA sequences or a set of sequence variations that may be used as bases for subsequent processing/comparisons, such as in deriving mutations strings and analyzing the DNA sample set 206 (FIG. 2).

For context, samples collected from patients may include fragments or portions of the overall DNA. As such, the corresponding sequenced values or the text string may include different combinations of characters. The processing system 102 (FIG. 1A) can generate the expected phrases 410 as representations of different character combinations that include the uniquely identifiable segments (e.g., the refined segment set 404 (FIG. 4A), such as the refined set of unique TRs).

Accordingly, the processing system 102 can generate the expected phrases 410 based on the refined segment set 404 instead of the initial segment set 402 (FIG. 4A). In some implementations, the processing system 102 can generate a set (illustrated as a unique sequence identifier number in FIG. 4) of the expected phrases 410 for each of the unique segments 360 (illustrated using bolded characters in FIG. 4) in the refined segment set 304.

The expected phrases 410 can have a phrase length 416 of k (e.g., between 10 to 50 or more) number of DNA base pairs or pairs of nucleobases. Each DNA base pair can be represented as a single text character (e.g., 'A' for adenine, 'C' for cytosine, 'G' guanine, and 'T' thymine). As such, the expected phrases 410 may also be referred to as "k-mers."

In some implementations, as described above, the unique segment 360 can include a DNA sequence, of a specified minimum length. The unique segment 360 can include a series of multiple instances of directly adjacent identical repeating nucleotide units or the repeated base units 356. For example, the unique segment 360 can include a minisatellite DNA or microsatellite DNA sequence of a specified minimum length. Accordingly, the unique segment 360 can correspond to a repeated pattern of the repeated base units 356, and the number of repetitions can correspond to a segment length 420 (e.g., the total length of, or total number of, nucleotide base pairs) for the unique segment 360. The repeated base unit 356 can have a base unit length 424 corresponding to the number of nucleotides within the repeated base unit 356 (e.g., one for a mono-nucleotide, two for a di-nucleotide, etc.).

For illustrative purposes, FIG. 4 shows a specific instance for the unique segment 360 of "AAAAAAAA," annotated as "A8," located at the molecular position starting at "10, 513,372" on chromosome 22. In this example, the unique segment 360 includes the segment length 420 of eight base pairs with the repeated base unit 356 of one base pair (e.g., a monomer or a mono-nucleotide) 'A.'

The processing system 102 can use the phrase length 416 (e.g., k between 10 to 50 or more base pairs) that has been predetermined or selected to capture targeted amount of data/characters surrounding the unique segments 360. As such, the phrase length 416 can be greater than the segment length 420, and each of the expected phrases 410 can include a set of flanking texts 414 (e.g., text-based patterns; illustrated using italics in FIG. 4) preceding and/or following the corresponding unique segment 360.

The processing system 102 can generate the expected phrases 410 in a variety of ways. As an illustrative example, the processing system 102 can use each of the unique segments 360 as an anchor for a sliding window having a length matching the phrase length 416. The processing system 102 can iteratively move the sliding window relative to the unique segment 360 and log the text captured within the window as an instance of the expected phrases 410. As such, each of the expected phrases 410 can correspond to a unique position of the sliding window relative to the unique segment 360. Also, the set of expected phrases 410 for one reference TR can include different combinations of the flanking text 414 (e.g., a combination of one or more leading characters 432 and/or one or more tailing characters 434.

The total number of base pairs in flanking text 414 can be a fixed value that is based on the phrase length 416 and the segment length 420. The number of characters in the flanking text can be calculated as the difference between the phrase length 416 and the segment length 420. As an example, for one of phrases having a length of 21 base pairs and a segment length of 8 base pairs, the flanking text can include 13 base pairs/characters.

Each of the expected phrases 410 can represent one of a number of position variant k-mers based on the flanking texts 414. The position variant k-mers can include specific numbers of base pairs in the expected flanking text 432 and tailing flanking text 434. For example, a set of the expected phrases 410 can include the same unique segment (e.g., repeated pattern of the TR) and differ from one another according to the number of base pairs included in the leading flanking text 432 and/or the tailing flanking text 434. In general, the number of base pairs included in the leading flanking text 432 and tailing flanking text 434 can vary inversely between the different instances of the position variant k-mers or expected phrases 410.

As an example, each of the expected phrases 410 illustrated in FIG. 4 has the phrase length 416 of 21 base pairs and the segment length 420 of 8 base pairs. A first expected phrase can have the leading characters 432 corresponding to 12 base pairs and the tailing character 434 corresponding to 1 base pair. A second expected phrase can have the leading characters 432 corresponding to 11 base pairs and the tailing characters 434 of 2 base pairs. The pattern can be repeated until the last expected phrase has the leading characters 432 corresponding to 1 base pair and the tailing characters 434 corresponding to 12 base pairs.

The expected phrases 410 can be grouped into sets that each correspond to a unique segment as described above. The total number of phrases or position variant k-mers (position variant total) in the grouped set can be represented as:

Position Variant Total=(Phrase length $k$)−(Segment length)−1.

For the example illustrated in FIG. 4, the set of expected phrases can have a position variant total of 12, representing 12 different instances of phrases corresponding to the phrase length 416 of 21 and the segment length 420 of 8.

In some implementations, the processing system 102 can use the unique instances of the TRs as the basis for generating the sets of expected phrases 410. Accordingly, each of the expected phrases 410 can also be unique since it is generated using the corresponding unique TR as a basis. The processing system 102 can use the unique expected phrases 410 to account for and identify the fragmentations likely to be included in the patient samples.

Base Text Patterns—Derived Phrases

The processing system 102 can use the expected phrases to analyzes mutations in genetic information (e.g., sequenced DNA segments), such as for detecting tumorous/cancerous DNA sequences. The expected phrases can be used to detect locations within the reference genome and related mutations that are indicative of certain types of cancers or likely onset thereof. The processing system 102 can use the expected phrases as basis to generate derived phrases that represent various mutations in the genetic information. The processing system 102 can use the derived phrases to recognize or detect mutations in the DNA sample set 206 (FIG. 2), the sample data 130 (FIG. 1A), or the like in developing, training, and/or deploying the ML model 104. Effectively, the processing system 102 can identify the mutation patterns indicative of certain types of cancers based on using the derived phrases to determine differences between healthy and cancerous DNA samples (between, e.g., the cancer-free data 210, the non-regional data 211, and/or the cancer-specific data 212 illustrated in FIG. 2).

Figure 5:
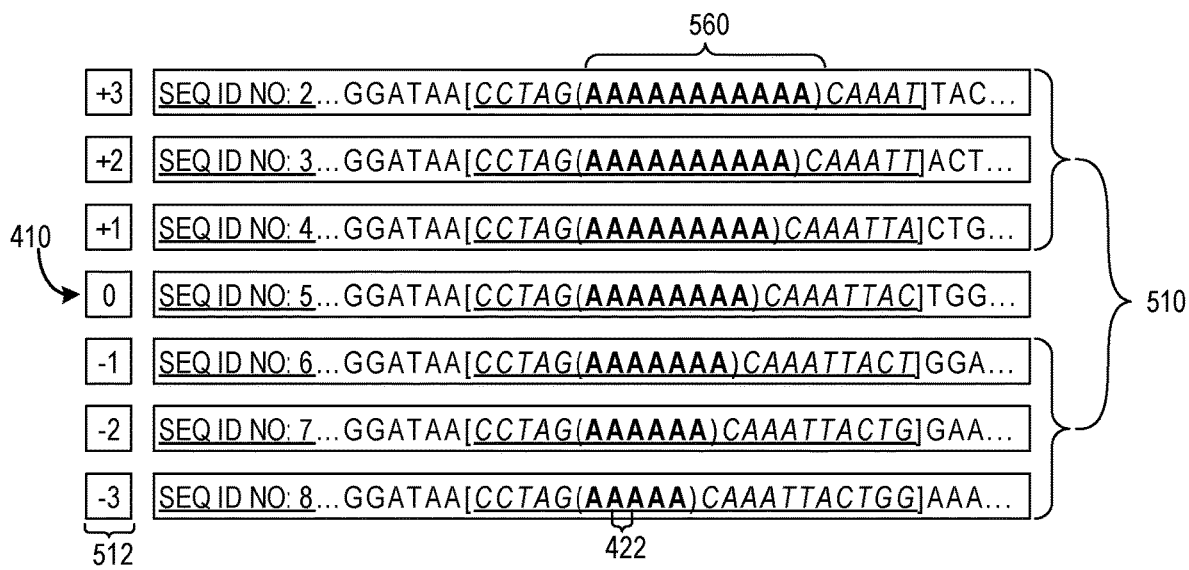
FIG. 5 shows example derived phrases in accordance with one or more implementations of the present technology.

FIG. 5 shows example derived phrases 510 in accordance with one or more implementations of the present technology. The processing system 102 (FIG. 1A) can generate the derived phrases 510 based on adjusting the expected phrases 410 expected to a predetermined pattern. For example, for one or more or each expected phrase 410, the processing system 102 can generate a set of the derived phrases 510 that represent indel mutations of the corresponding expected phrase 410. In some implementations, the processing system 102 can generate the set of derived phrases 510 that correspond to a predetermined number of insertions and/or deletions in the unique segment 360 (FIG. 4) within the corresponding expected phrase 410. In other words, the set of derived phrases 510 can represent the indel variants of the sequence represented by the corresponding expected phrase 410.

The processing system 102 can generate the set of the derived phrases 510 based on adjusting (via insertion/deletion) the number of the repeated base units 356 (FIG. 4) and/or one or more characters in the unique segment 360 of the expected phrase 410. Accordingly, the processing system 102 can generate a set of derived segments 560 that correspond to indel variants of the unique segment 360.

The processing system 102 can generate the derived phrases 510 based on adding and/or adjusting the flanking text 414 (FIG. 4) around the derived segments 560 (illustrated as the bolded characters within parentheses '( )'). In some implementations, the processing system 102 can generate the derived phrases 510 having the same phrase length 416 (FIG. 4) as the expected phrases 410. As a result, the processing system 102 can expand or reduce the coverage of the flanking text 414 according to the indel changes to the unique segment 360 (e.g., the originating pattern of TRs). With deletions, the processing system 102 can include corresponding number of new characters from the overall sequence into the flanking text 414 (FIG. 4). Similarly with additions, the processing system 102 can remove the corresponding number of characters from the flanking text 414. For illustrative purposes, FIG. 5 shows the surrounding adjustments occurring in the trailing characters 434 (FIG. 4) while maintaining the leading characters 432 (FIG. 4). However, it is understood that the processing system 102 can operate differently, such as by (1) adjusting the leading characters 432 while maintaining the trailing characters 434 and/or (2) spreading the adjustments across the leading characters 432 and the trailing characters 434 according to the number of characters in the original phrase and/or a predetermined pattern.

For the example illustrated in FIG. 5, the expected phrase 410 can correspond to the repeated TR segment of "AAAAAAAA" or A8 beginning at position 10,513,372 on chromosome 22. The derived phrases 510 can correspond to the derived segments 560 including up to three insertions and deletions of the repeated base unit 'A.' In other words, the derived phrases 510 can correspond to phrases built around A5, A6, A7, A9, A10, and A11.

The number of the derived phrases 510 associated with a given expected phrase can be determined by an indel variant value 512. The indel variant value 512 can include an integer value representative of the number of insertions and deletions. The indel variant value 512 can further function as an identifier for a phrase. For example, the indel variant value '0' can represent the expected phrase 410 having zero insertions/deletions. Positive indel variant values (e.g., 1, 2, 3) can represent derived phrases including corresponding number of insertions of base units or characters in the repeated TR portion. Negative indel variant values (e.g., −1, −2, −3) can represent derived phrases corresponding number of deletions of base units or characters in the repeated TR portion. For the example illustrated in FIG. 5, the indel variant values 1, 2, and 3 can represent/identify A9, A10, and A11, respectively. Also, the indel variant values −1, −2, and −3 can represent A7, A6, and A5, respectively.

For context, the processing system 102 can use the expected phrases 410 and the corresponding sets of derived phrases 510 to analyze the DNA sample set 206 and develop/test the ML model 104 (FIG. 1A). The phrases generated using the unique TR patterns can provide accurate and precise identification of corresponding sequences in the different types of health and cancerous DNA samples. In other words, the various phrases can represent the type of textual patterns or the corresponding sequences that are targeted for analyses and comparisons between the cancer-free data 210, the non-regional data 211, and/or the cancer-specific data 212. For example, the processing system 102 can use the various phrases to identify the numbers and types/locations of mutations in the cancer-related samples and absent in healthy samples. The processing system 102 can aggregate the results across multiple samples and patients to derive a pattern or a correlation between certain types of mutations and the onset of certain types of cancer.

To put things another way, the processing system 102 can identify unique patterns (e.g., the unique TR patterns and/or the corresponding expected phrases 410) that each occur once within the human genome. The unique patterns can be used to identify specific locations and portions within the human genome for various analyses. Moreover, the processing system 102 can target specific types of mutations, such as indel mutations, in developing a cancer-screening and/or a cancer-predicting tool. It has been found that various types of cancers can be accurately detected and progress/status of such types of cancers can be described using the expected phrases 410 and the corresponding sets of the derived phrases 510 (e.g., sequences identified using unique TR-based patterns and indel variants thereof) and without considering other aspects/mutations of the human DNA. As a result, the processing system 102 can generate the ML model 104 that can accurately detect the existence, predict a likely onset, and/or describe a progress of certain types of cancers using the various phrases. In other words, the processing system 102 can detect/predict the onset of cancer without processing the entire DNA sequence and different types of mutation patterns.

The processing system 102 can further improve the efficiency and reduce the resource consumption using the indel variant value 512. Given the downstream processing methodology, the indel variant value 512 can control the number of phrases considered in developing/training the ML model 104 and thereby affect the overall number of computations and the amount of resource consumption. When the indel variant value 512 is too high, the processing system 102 may end up analyzing a reduced or ineffective number of possible sequences. For example, as the total number of base pairs in the TR indel variant approaches the phrase length 416, the number of available derived phrases and the likely occurrence of such mutations decrease. Accordingly, in some implementations, the indel variant value 512 in the range of three to five provides sufficient coverage for varying degrees of possible insertion and deletion mutations that are indicative of one or more types of cancer. This range of values may be sufficient to provide accurate results without requiring ineffective or inefficient amount of computing resources.

Additionally, the processing system 102 can further improve the efficiency and reduce the resource consumption using the segment length 420 (e.g., the length of the uniquely identifiable TR-based pattern). It has been found that the probability of mutation occurrences decreases as the tandem repeat segment length 420 is reduced. In particular, the mutation rate for genome TR sequences with segment length 420 of fewer than five base pairs is significantly less than genome TR sequences with the segment length 420 of five or more base pairs. Thus, the expected phrases 410 can be selected as the genome TR sequence with the segment length 420 of five or greater.

Base Text Patterns—Storage/Trackinq

Figure 6:
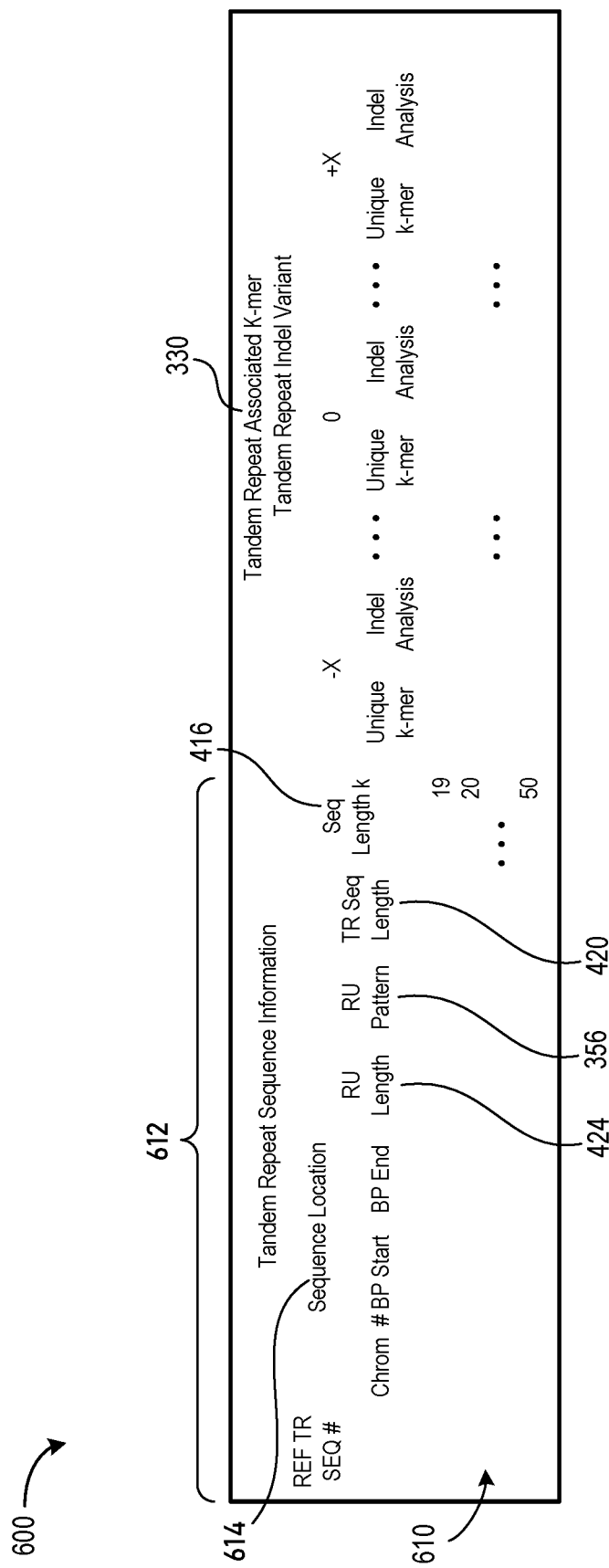
FIG. 6 shows an example analysis template in accordance with one or more implementations of the present technology.

The processing system 102 can store the various phrases (e.g., the expected phrases 410 and/or the corresponding sets of the derived phrases 510) in the genome TR reference catalogue 230 (FIG. 2). FIG. 6 shows an example analysis template 600 in accordance with one or more implementations of the present technology. The processing system 102 can use the analysis template 600 to represent the various phrases and/or track the associated processing results.

In some implementations, the analysis template 600 can correspond to a format for the genome TR reference catalogue 230. The genome TR reference catalogue 230 can include catalogue entries 610 for each instance of the unique segments 360 (e.g., uniquely identifiable or reference TR patterns). The entries 610 can include TR sequence information 612 that characterizes the unique segments 360 and/or the derived segments 560. For example, the TR sequence information 612 can include a sequence location 614, the segment length 420, the base unit length 424, the repeated base unit 356, or a combination thereof.

The sequence location 614 can identify the location of the corresponding unique segment 360 and/or expected phrase 410 within the reference genome. As an example, the sequence location 614 can be described based on the molecular location of the unique segment 360, such as (1) the chromosome on which the TR sequence is located and/or (2) the base pair numbers in the chromosome marking the beginning/end of the TR sequence. The sequence location 614 can act as a unique identifier that distinguishes one instance of the unique segment 360 and/or the expected phrase 410 from another. For example, the expected phrase s410 that share the same repeated base unit 356 and the base unit length 424 can be distinguished from one another based on the sequence location 614.

The entries 610 for each instance of the unique segment 360 can include information for one or more instances of the corresponding phrases (e.g., expected and/or derived). For example, the entries 610 can include information for the expected phrases 410 and/or the derived phrases 510 with various values for the phrase length 416. For illustrative purposes, this instance of entries 610 is shown including information for the expected phrases 410 with phrase lengths corresponding from 19 base pairs to 60 base pairs. However, it is understood that the entries 610 can include information regarding fewer than 19 base pairs and/or more than 60 base pairs. As another example, the entries 610 can include information that distinguishes between the expected phrases 410 and the derived phrases 510. In some implementations, the entries 610 can identify the expected phrases 410 associated with a corresponding TR pattern. For instance, the TR pattern A8 beginning at position 10,513,372 can yield 16 sequences or expected phrases 410 having the phrase length 416 of 30 base pairs.

The entries 610 can further identify the derived phrases 510 that are absent from the reference genome. For illustrative purposes, Table 1 below summarizes the derived phrases 510 having the segment length 416 of 30 base pairs for the unique segment 360 or TR pattern of "A8" beginning at position 10,513,372 (annotated as '372) on chromosome 22. In this example, each of the derived phrases 510 corresponding to indel variants with the indel variant value 512 ranging from "−5" to "+5" are not found in the reference genome.

TABLE 1

Chromosome 22, '372, "A8" Reference
TR Associated Indel Phrase Summary

| Indel Variant Value | Position Variant Total | Total That Do Not Appear |
|---|---|---|
| +5 | 16 | 16 |
| +4 | 17 | 17 |
| +3 | 18 | 18 |
| +2 | 19 | 19 |
| +1 | 20 | 20 |
| −1 | 22 | 22 |
| −2 | 23 | 23 |
| −3 | 24 | 24 |
| −4 | 25 | 25 |
| −5 | 26 | 26 |

The analysis template 600 can be used to track the statistical data generated during development/training of the ML model 104. For example, the processing system 102 can track the occurrences of certain mutations according to the sequence location 614 or the identifier for the corresponding entry 610 and the indel mutation offset/identifier. The processing system 102 can use the counted occurrences for each sample, each sample set, or a combination thereof to compute the correlation between the mutations and the onset of the corresponding type of cancer.

In some embodiments, the processing system 102 can calculate the number of occurrences for each of the expected and/or derived phrases, such as for indel variants with or without indel variant '0', in the patient sequencing data. For each set of phrases associated with a particular indel variant type, the processing system 102 can calculate a statistical value (e.g., a median value) from the set of the number of occurrences. The median value can represent the counts associated with the particular TRS with a particular type of indel variant in the corresponding patient.

As an illustrative example, the processing system 102 can process three TRSs derived from a targeted k=16 wild type nucleotide (e.g., ATCATCATC) as shown below.

| TRS<br>Associated Kmers (underlined) | SEQ<br>ID NO | Kmer<br>count |
|---|---|---|
| ...ACTTGA*ATCATCATCATC*CTCCTA... | 10 | 7 |
| ...ACTTGA*ATCATCATCATC*CTCCTA... | 11 | 11 |
| ...ACTTGA*ATCATCATCATC*CTCCTA... | 12 | 10 |

The processing system 102 can calculate the median value of the counts as 10. Accordingly, the processing system 102 can assign a count of 10 to a corresponding TRS indel type (e.g., indel type+1) for this patient.

The analysis template 600 is shown for exemplary purposes as a template with a general layout for organizing information for each of the segments and/or phrases. It is understood that the analysis template 600 can include different categorizations and arrangements with additional or different pieces of information. Further, it is understood that an active or "in use" version of the genome TR reference catalogue 230 can be populated with values corresponding to the various categories of the entries 610.

Duplicate Filtering

In addition to carefully selecting the processing parameters (e.g., the indel variant value 512 and/or the segment length 420) and reducing the overlaps 352 in the unique segments 360 described above, the processing system 102 can further increase the processing efficiencies and accuracy of the ML model 104 by removing duplicate phrases or k-mers. The processing system 102 can inadvertently introduce or generate the duplicate phrases since the derived phrases 510 are generated by altering the unique segments 360. In other words, the derived phrases 510 may include character sequences that match other phrases corresponding to other portions of the human genome (e.g., derived and/or unique phrases corresponding to different locations/TR combinations). The processing system 102 can use the refinement mechanism 115 (e.g., the duplicate filter 254 (FIG. 2)) to identify and remove such duplicated phrases.

In some implementations, the duplicate filter 254 can be configured to compare the derived phrases 510 to the expected phrases 410 corresponding to different locations in the human genome. Additionally or alternatively, the duplicate filter 254 can be configured to compare the derived segments 560 to the unique segments 360 associated with other locations. Moreover, the duplicate filter 254 can compare the derived phrases 510 and/or derived segments 560 across different locations to find matches. For example, the processing system 102 can sort the phrases according to the unique segments 360 and/or the repeated base unit 356 and then according to the base unit length 424. The duplicate filter 254 can be configured to remove one or more or all instances of the matching phrases (having, e.g., same base TR units and TR-pattern length). In other words, the duplicate filter 254 can remove from further processing character combinations representative of sequences/mutations that can be found at multiple locations in the human genome. Accordingly, the processing system 102 can ignore the potentially misleading character patterns in analyzing for correlations to different types of cancers and reduce the overall number of processed phrases.

Downstream Filtering

In addition to the text-based filtering described above, the processing system 102 can further filter the data and/or the processing results. For example, the processing system 102 can use the quality filter 256 (FIG. 2) to preprocess and/or adjust for the input patient data, such as the DNA sample set 206. The processing system 102 can use the quality filter 256 to reduce, remove, or adjust for imperfections (e.g., biases caused by inaccurate/insufficient reads) that may be introduced by sequencing technologies. In some implementations, the quality filter 256 can adjust for or normalize different read depths (e.g., the number of times that a given nucleotide in the genome was detected in a sample) across the separately sequence data, such as across the cancer-free data 210, the non-regional data 211, and/or the cancer-specific data 212.

To adjust for the different read depths, the quality filter 256 can be configured to require minimum read depths for the input data. In other words, the quality filter 256 can remove or filter out samples and/or corresponding sequenced strings having the sample read depth 214 (FIG. 2) less than a predetermined threshold (e.g., 10). Additionally or alternatively, the quality filter 256 can be configured to normalize the read depths to a predetermined depth (e.g., 200) across the different data sets. In normalizing the read depth, the quality filter 256 can calculate a scale factor for each data set by dividing the predetermined depth by the corresponding sample read depth 214. The scale factor can be applied or multiplied to wild type counts (e.g., number of character sequences/segments corresponding to genes found in natural non-mutated form) for the set, thereby calculating the normalized wild type count. Similarly, the quality filter 256 can apply the scale factor to the mutation counts (e.g., indel counts) found in each corresponding set. Accordingly, the wild type counts and the mutations counts for the different data sets can be normalized to a common predetermined read depth using the scale factor.

Separately or additionally, the quality filter 256 can be configured to remove nucleotides having sub-standard quality. For example, the quality filter 256 can be configured to filter out data samples or strings having the sample quality score 216 (FIG. 2), such as the phred quality score, below a predetermined quality threshold (e.g., 20). The quality filter 256 can replace characters for the substandard nucleotides to a predetermined character (e.g., 'N').

The processing system 102 can further use the comparison correction filter 258 (FIG. 2) to remove computational noise or errors. Even with the reduced number of computations, the number of computations and comparisons may inadvertently introduce false positives. Accordingly, the comparison correction filter 258 can be configured to correct the intermediate data, such as using a Bonferroni correction process. For example, the comparison correction filter 258 can adjust (by, e.g., dividing) a predetermined somatic classification threshold (p-value criteria, such as 0.01) by the number of phrases being processed/compared.

Moreover, the processing system 102 can use the fraction filter 260 (FIG. 2) to remove or adjust for physiological and/or collection-based features that interfere with the data processing. In some implementations, the fraction filter 260 can be configured to address samples having relatively low numbers of derived phrases (e.g., sample sets having mutant counts less than a predetermined threshold). For example, the fraction filter 260 can include an allelic fraction filter. The allelic fraction for sample/data can be calculated based on dividing the number of derived phrases by a sum of wild type counts and mutant counts. The fraction filter 260 can classify data/strings as not being somatic when the corresponding allelic fraction values are less than a predetermined threshold (e.g., 0.05).

Figure 7:
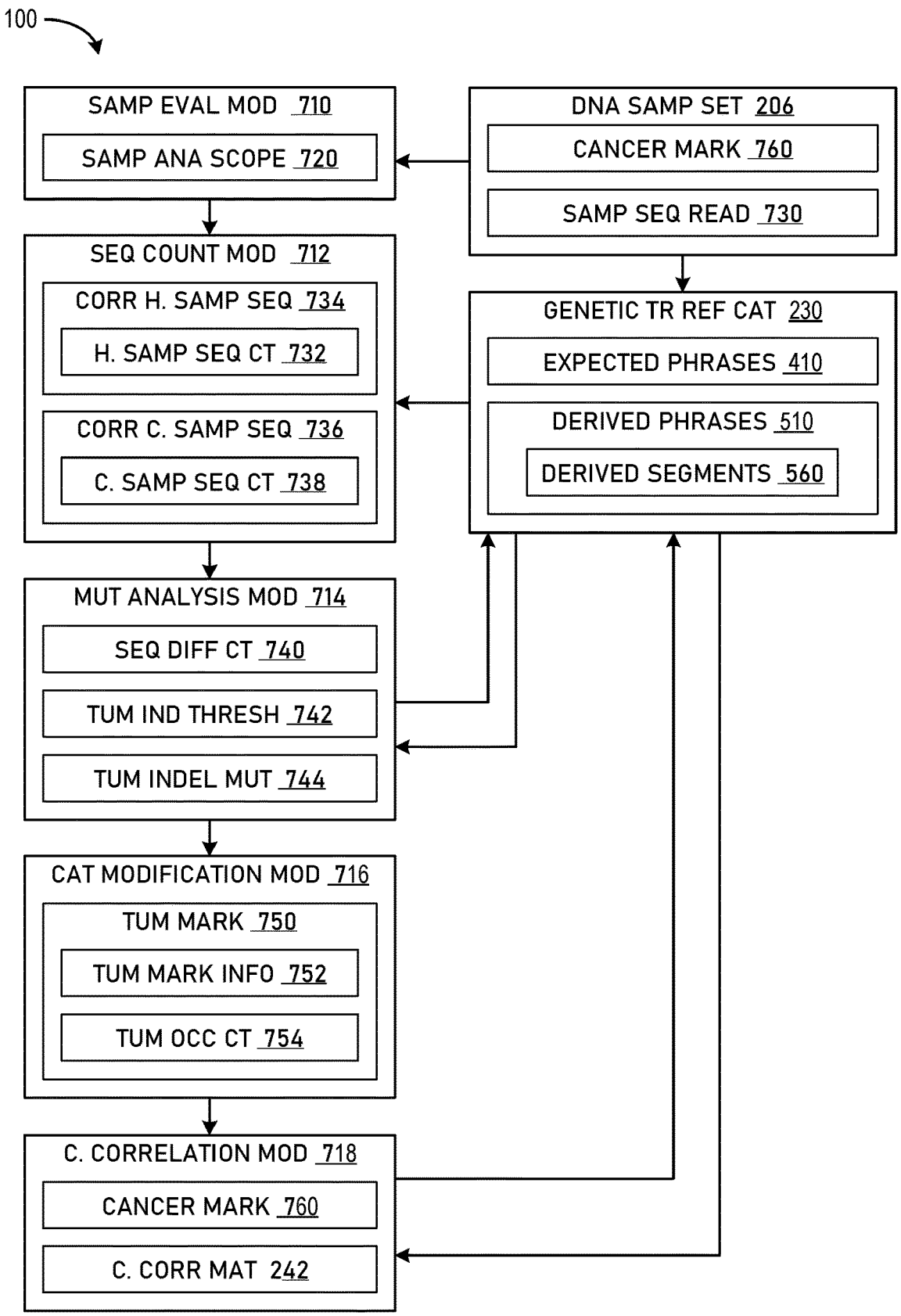
FIG. 7 shows an example control flow diagram illustrating the functions of the system in accordance with one or more implementations of the present technology.

FIG. 7 shows a control flow diagram illustrating the functions of the computing system 100 in accordance with various embodiments. The computing system 100 can be implemented to supplement and refine information in the genome TR reference catalogue 230 with information from the DNA sample sets 206 based on the unique segments 360 and the various phrases. In general, the computing system 100 can analyze one or more of the DNA sample sets 206 to process (1) mutations at specific locations of DNA sequences, (2) correlation of mutation patterns, (3) corresponding indications of one or more types of cancer, or a combination thereof. The functions of the computing system 100 can be implemented with a sample set evaluation module 710, a sequence count module 712, a mutation analysis module 714, a catalogue modification module 716, a cancer correlation module 718, or a combination thereof.

The evaluation module 710 can be configured evaluate the scope of the DNA sample set 206, including the cancer-free data 210, the non-regional data 211, and/or the cancer-specific data 212. For example, the evaluation module 710 can evaluate the DNA sample set 206 to identify factors, properties, or characteristics thereof to facilitate analysis of the different categories of data. In some implementations, the evaluation module 710 can be optional. The evaluation module 710 can generate a sample analysis scope 720 for the DNA sample set 206. The sample analysis scope 720 is a set of one or more factors that may govern/control the analysis of the DNA sample set 206. For example, the sample analysis scope 720 can be generated based on the supplemental information 220. The sample analysis scope 720 can be used to identify usable phrases (e.g., the expected phrases 410 and/or the derived phrases 510) based on the sequence location 614 and the phrase length k 416.

The computing system 100 can receive the derived phrases 510 and associated information from the genome TR reference catalogue 230 and/or the DNA sample set 206. The mutation analysis mechanism can be implemented with the count module 712 and the analysis module 714. The count module 712 may be responsible for calculating a number of occurrences (e.g., a sequence count) for specific DNA sequences/phrase in a sample set. The count module 712 can calculate the sequence count based on a number of sample sequence reads 730, such as the sequence reads for the DNA fragments in one or more categories of data in the DNA sample set 206.

For the cancer-free data 210, the count module 712 can calculate a healthy sample sequence count 732 for each instance of a corresponding healthy sample sequence 734 identified in the cancer-free data 210. The corresponding healthy sample sequence 734 is a DNA sequence in the healthy sample DNA information 734 that corresponds to one of the derived segments 560 and/or the derived phrases 510. The heathy sample sequence count 732 is the number of times that the corresponding healthy sample sequence 734 is identified in the cancer-free data 210. Similarly, for the cancer-specific data 212 and/or the non-regional data 211, the count module 712 can calculate count values for each instance of a targeted sequence identified in the data group. In other words, the count module 712 can calculate the number of times the various phrases are found within the samples according to the corresponding groups/categories.

The count module 712 can identify the corresponding healthy sample sequence 734 and the corresponding cancerous sample sequence 738 for a given expected phrase, and more specifically the derived phrase. For example, the sequence count module 712 can search through the different categories of data for matches to one or more of the derived segments within the corresponding phrases. As one specific example, the count module 712 can search for a string of consecutive base pairs that matches one of the derived segments 560 of the derived phrases 510.

The count module 712 can calculate the healthy sample sequence count 732 as the total number of each of the corresponding healthy sample sequence 734 identified in each of the sample sequence reads 730 in the cancer-free data 210. In many cases, the corresponding healthy sample sequence 734 will correspond with a single instance of the tandem repeat indel variants 310. In these cases, the total value of the healthy sample sequence count 732 will be equal to the total number of the sample sequence reads 730 in the cancer-free data 210. For example, where the cancer-free data 210 includes 50 instances of the sample sequence reads 730 per DNA segment, the healthy sample sequence count 732 for a given instance of the corresponding healthy sample sequence 734 should also be 50. The case of non-unity between the number of sequencing reads and the healthy sample sequence count 732 can generally be attributed to sequencing errors.

In many cases, the corresponding healthy sample sequence 734 will match with the phrase with the indel variant value 312 of zero (e.g., the expected phrase with no insertions or deletions of the unique segment 360). However, in some cases, the corresponding healthy sample sequence 734 can differ. The differences between the corresponding healthy sample sequence 734 and the phrase with the indel variant value 312 of zero can account for wild type variants (e.g., naturally occurring variations) in the cancer-free data 210.

Similarly, the count module 712 can calculate the cancerous sample sequence count 736 for each of the corresponding cancerous sample sequence 738 that appear in the sample sequence reads 730 in the cancer-specific data 212. Due to possible mutations, the cancer-specific data 212 can include multiple different instances of the corresponding cancerous sample sequence 738 matching different instances of the derived segments 560, with each corresponding cancerous sample sequence 738 having varying values of the cancerous sample sequence count 736. As an example, in some cases, the corresponding cancerous sample sequence 738 and cancerous sample sequence count 736 will match with the corresponding heathy sample sequence count 734 and healthy sample sequence count 732, indicating no mutations. As another example, for a given instance of the derived phrase 510, the cancer-specific data 212 may have a split in the cancerous sample sequence count 736 between the cancerous sample sequence 738 that is the same as the corresponding healthy sample sequence 734 and one or more other instances of the tandem repeat indel variants 310. For a given instance of the derived phrase 510, the count module 712 can track the cancerous sample sequence count 736 for each different instance of the corresponding cancerous sample sequence 738 in the cancer-specific data 212.

The flow can continue to the analysis module 714. The analysis module 714 may be responsible for determining whether a mutation exists in the corresponding cancerous sample sequence 738 of the cancer-specific data 212. In general, the existence of a mutation in the cancer-specific data 212 can be determined based on differences in the repeated TR patterns between the corresponding heathy sample sequence 734 and the corresponding cancerous sample sequence 738. More specifically, a difference in the number of the repeated base unit 356 can represent the existence of an indel mutation (e.g., a mutation corresponding to an insertion or a deletion of the repeated TR unit), such as for cancer-specific data 212 in comparison to the cancer-free data 210. For example, the analysis module 714 can determine that a mutation exists when the corresponding cancerous sample sequence 738 matches one of the derived segments 560 and/or the derived phrases different from that of the corresponding healthy sample sequence 734. In another example, the analysis module 714 can determine the difference between the corresponding healthy sample sequence 734 and the corresponding cancerous sample sequence 738 based on a sequence different count 740 (e.g., the total number of corresponding cancerous sample sequences 738 differing from the corresponding healthy sample sequences 734). In the case where the sequence difference count 740 indicates no differences, such as when the sequence difference count 740 is zero, the analysis module 714 can determine that no mutation exists in the corresponding cancerous sample sequence 738.

In general, the analysis module 714 can determine that an indel mutation has occurred when the sequence difference count 740 is a non-zero value. In some embodiments, the analysis module 714 determines whether the indel mutation is a tumorous indel mutation based on whether the sequence difference count 740 is greater than the error percentage of the approach or apparatus used to sequence the cancer-free data 210, cancer-specific data 212, or a combination thereof.

In another implementation, the analysis module 714 can determine whether the indel mutation is a tumorous indel mutation 744 based on a tumor indication threshold 742. The tumor indication threshold 742 is an indicator of whether the number of mutations for a particular sequence in the cancer-specific data 212 indicates the existence of a tumorous indel mutation 744. The tumorous indel mutation 744 may occur when the sequence difference count 740 exceeds a tumor indication threshold 742. As an example, the tumor indication threshold 742 can be based on a percentage between the total number of sample sequence reads 730 and the sequence difference count 740. As a specific example, the tumor indication threshold 742 can require a sequence different count 740 to be greater than 70 percent of the sample sequence reads 730 for the cancer-specific data 212. In another specific example, the tumor indication threshold 742 can require the sequence difference count 740 to be greater than 80 percent of the sample sequence reads 730 for the cancer-specific data 212. In another specific example, the tumor indication threshold 742 require the sequence difference count 740 to be greater than 90 percent of the sample sequence reads 730 for the cancer-specific data 212.

When the corresponding cancerous sample sequence 738 includes the tumorous indel mutation 744, the computing system 100 can implement the modification module 716 to update or modify the genome TR reference catalogue 230. Said another way, the computing system 100 can implement the modification module 716 responsive to determining that the corresponding cancerous sample sequence 738 includes the tumorous indel mutation 744. For example, the modification module 716 can modify the genome TR reference catalogue 230 by identifying the instance of the catalogue entries 610 as a tumor marker 750 when the tumorous indel mutation 744 exists in the corresponding cancerous sample sequence 738.

The catalogue entries 610 that are identified as a tumor marker 750 can be modified by the modification module 716 to include tumor marker information 752. Some examples of the tumor marker information 752 can include a tumor occurrence count 754, such as the number of times that the tumorous indel mutation 744 was identified in a particular instance of the segment/phrase (e.g., TR pattern) for a given form of cancer. As a specific example, the tumor occurrence count 754 can be compiled from analysis for the DNA sample sets 206 for numerous cancer patients.

In another example, the tumor marker identification 752 can include information about the different instances of the corresponding cancerous sample sequence 738 matching to different instances of the derived segments/phrases along with the cancerous sample sequence count 736, the total number of sample sequence reads 730 of the DNA sample set 206, all or portions of the supplemental information 220, or a combination thereof. In a further example, the tumor marker information 752 can include the number of repeated base units 356 in the corresponding cancerous sample sequence 738 that were different from the corresponding healthy sample sequence 734.

The tumor marker information 752 can include information based on the supplemental information 120. For example, the tumor marker information 752 can include the supplemental information 220 (e.g., source information), such as the cancer type, the stage of cancer development, organ or tissue from which the sample was extracted, or a combination thereof. In another example, the tumor marker information 752 can include the supplemental information 220 of the patient demographic information, such as the age, the gender, the ethnicity, the geographic location of where the patient resides or has been, the duration of time that the patient stayed or resided at the geographic location, predispositions for genetic disorders or cancer development, or a combination thereof.

The computing system 100 can use one or more instances of the segments/phrases identified as the tumor marker 750 to generate the cancer correlation matrix 242 with the correlation module 718. For example, the correlation module 718 can identify cancer markers 760 based on the tumor occurrence count 754 for each of the tumor markers 750 in the genome TR reference catalogue 230. The cancer markers 760 can correspond to mutation hotspots that are specific to indel mutations in instances of the TR patterns. In one implementation, the correlation module 718 can identify the cancer markers 760 based on regression analysis. For example, the regression analysis can be performed with a receiver operating characteristic curve to the optimum sensitivity and specificity from the tumor markers 750, tumor occurrence count 754, or a combination thereof to determine the cancer markers 760.

In another implementation, the correlation module 718 can identify the cancer markers 760 based on a ratio between, or percentage of, the tumor occurrence count 754 for the tumor marker 750 and the total number of the DNA sample sets 206 of a particular form of cancer that have been analyzed for the tumor marker 750. As a specific example, the correlation module 718 can identify the cancer markers 760 as the tumor markers 750 when the ratio between the tumor occurrence count 754 and the total number of DNA sample sets 206 that are analyzed is 90 percent or more of the DNA sample sets 206 for a particular form of cancer. In this case, the cancer correlation matrix 242 can include the cancer markers 760 that were identified in this manner.

In a further implementation, the correlation module 718 generates the cancer correlation matrix 242 as THE tumor markers 750 that are common among a percentage of the DNA sample sets 206 for a particular form of cancer are found. For example, the correlation module 718 can generate the cancer correlation matrix 242 as the tumor markers 750 appear in 90 percent or more of the total number of DNA sample sets 206. In other implementations, the correlation module 718 can generate the cancer correlation matrix 242 through other methods, such as regression analysis or clustering.

The correlation module 718 can generate the cancer correlation matrix 242 taking into account the supplemental information 220, such as the patient demographic information, to generate the cancer correlation matrix 242 for sub-populations. For example, the correlation module 718 can generate the cancer correlation matrix 242 based on the patient demographic information specific to gender, nationality, geographic location, occupation, age, another characteristic, or a combination of characteristics.

The computing system 100 has been described in the context of modules that perform, serve, or support certain functions as an example. The computing system 100 can partition or order the modules differently. For example, the evaluation module 710 could be implemented on the processing system 102, while the count module 712, analysis module 714, and correlation module 718 could be implemented on an external device. Alternatively, the processing system 102 can include the various modules described above.

The computing system 100 can implement the refinement mechanism 115 (FIG. 1A) via one or more or different modules described above. For example, the computing system 100 can include/implement the quality filter 256 in the sample evaluation module 710. Also, the computing system 100 can include/implement the consecutive overlap filter 252 and/or the duplicate filter 254 in the count module 712 (e.g., before or in preparation for the counting operations described above). Moreover, the count module 712 and/or the analysis module 714 can include the comparison correction filter 258 and/or the fraction filter 260.

Figure 8:
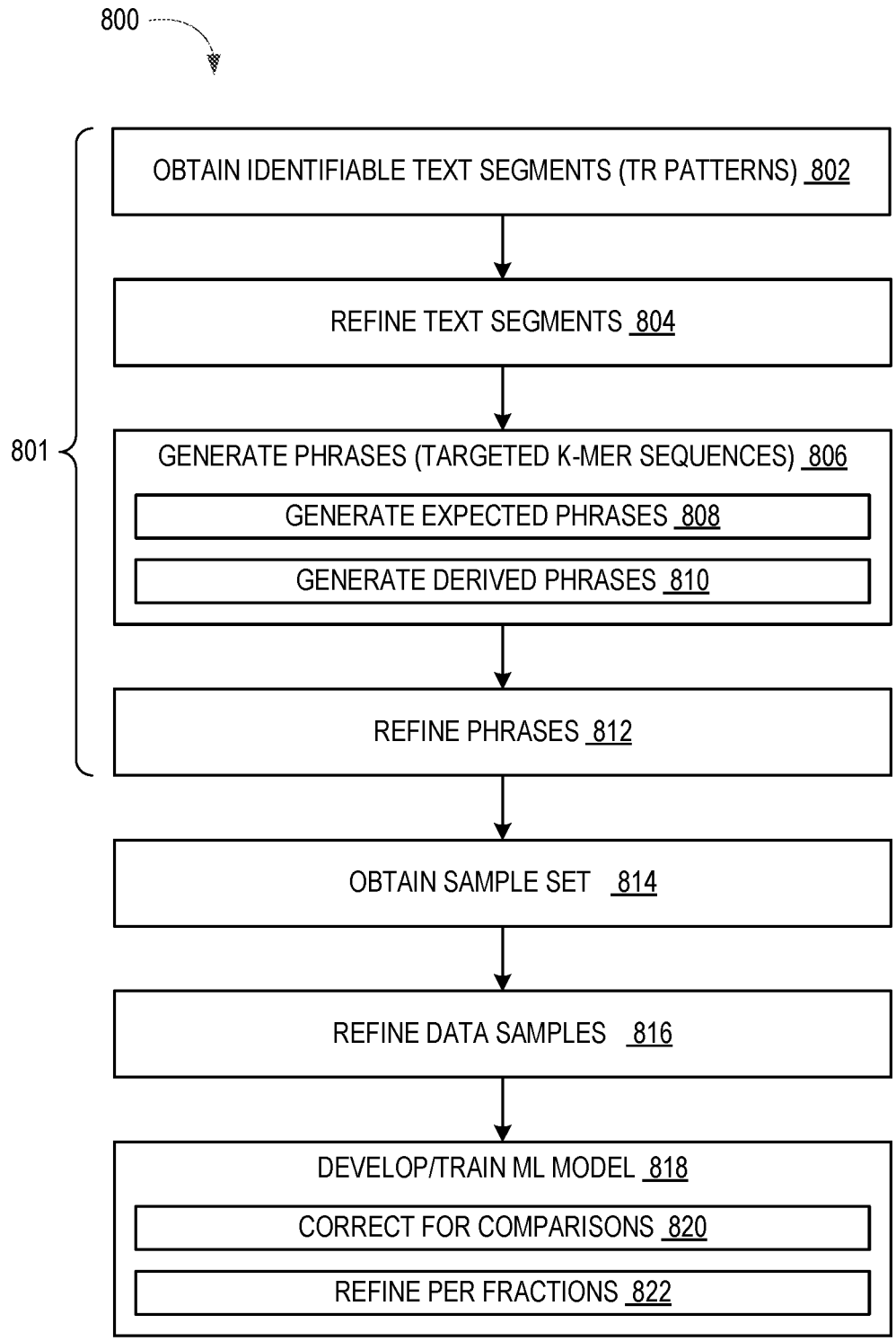
FIG. 8 shows a flow chart of a method for processing and refining DNA-based text data for cancer analysis in accordance with one or more implementations of the present technology.

FIG. 8 shows a flow chart of a method 800 for processing and refining DNA-based text data for cancer analysis in accordance with one or more implementations of the present technology. The method 800 can be implemented using the computing system 100 (FIG. 1A) including the processing system 102 (FIG. 1A). The method 800 can be for developing the ML model 104 (FIG. 1) including generating the various phrases and refining the processing results (via, e.g., the refinement mechanism 115 (FIG. 1)) as described above.

The method 800 includes the computing system 100 obtaining identifiable text sequences (e.g., TR-based patterns) at block 802. In some implementations, the processing system 102 can obtain the identifiable text sequences based on generating the unique segments 360 (FIG. 3) from the reference data 112 (FIG. 1A), such as by generating the character patterns representative of the identifiable TR patterns the human genome. In other implementations, the processing system 102 can access/receive the unique segments 360 generated by an external system/device.

The obtained unique segments 360 can serve as an initial set of segments representative of TR sequences. Each segment in the initial set can include N number of adjacently repeated base units 356. The repeated base units 356 for the initial set can have the base unit length 424 that is uniform across the segments.

At block 804, the computing system 100 can refine the identifiable text segments, such as by using/implementing the consecutive overlap filter 252 (FIG. 2). In some implementations, the processing system 102 can refine the identifiable text segments by removing the overlaps 352 (FIG. 3A), such as the TR patterns that are consecutive of and/or overlap each other, from the initial set of the unique segments 360 as described above. The processing system 102 can generate a refined set of the segments based on removing the overlaps 352 from the initial set.

At block 806, the computing system 100 can generate the phrases, such as the k-mer sequences targeted for use in subsequent data processing. For example, at block 808, the processing system 102 can generate the expected phrases 410 (FIG. 4). The processing system 102 can use the unique segments 360 (e.g., uniquely identifiable TR patterns) to generate the expected phrases 410, such as by adding different combinations of the flanking text 414 (FIG. 4) as described above. Also, at block 810, the processing system 102 can generate the derived phrases 510 (FIG. 5). The processing system 102 can use the expected phrases 410 to generate the derived phrases 510, such as by adjusting the unique segments 360 within the expected phrases to the derived segments 560 representative of indel mutations as described above.

In some implementations, the generated phrases can serve as an initial set. The generated phrases can correspond to different locations within the human genome. For example, the phrases can have the phrase length k 416 and include (1) location-specific TR-based segments (e.g., expected phrases 410) and/or (2) indel derivations of the TR-based segments adjacent to corresponding sets of flanking texts (e.g., derived phrases 510).

At block 812, the computing system 100 can refine the set of phrases, such as by using/implementing the duplicate filter 254 (FIG. 2). For example, the processing system 102 can refine the expected phrases 410 and/or derived phrases 510 by removing the duplicates or representations of DNA sequences or mutations that may correspond to more than one location. In other words, the processing system 102 can search for inadvertently generated representations of mutations that match mutations or expected/healthy sequences corresponding to a different location in the human genome as described above.

The operations described above for one or more of the blocks 802-812 can correspond to a block 801 for generating text phrases that represent different DNA sequences. The generated text phrases can represent various uniquely identifiable DNA sequences and mutations sequences for TR indel variants. The generated/refined text phrases can be used to determine correlations between the various mutations and onset cancer in the DNA sample set 206.

At block 814, the computing system 100 can obtain one or more sample sets (e.g., the DNA sample set 206 (FIG. 2)). In some implementations, the processing system 102 can receive sequenced DNA data from publicly available databases, healthcare providers, and/or submitting patients. The obtained data sample sets can include corresponding or known diagnoses, such as categorizations or tags identifying that the DNA data is from patients confirmed to be without cancer or confirmed to have specific cancers. Additionally, the obtained data can include physiological source locations of the DNA data. For samples sourced from the patients having cancer, the source locations can be the cancerous tumor or a location different from or unrelated to the malignant tumors. Accordingly, the processing system 102 can include a combination of the cancer-free data 210, the non-regional data 211, and the cancer-specific data 212, illustrated in FIG. 2. The obtained DNA sample set 112 can further include other details, such as the supplemental information 220 (FIG. 2), the sample read depth 214 (FIG. 2), the sample quality score 216 (FIG. 2), or the like.

At block 816, the computing system 100 can refine the data samples 816, such as by using/implementing the quality filter 256 (FIG. 2). For example, the processing system 102 can identify the characters corresponding to nucleotides having phred scores less than the quality threshold. The processing system 102 can replace the identified characters with a predetermined dummy letter as described above. Additionally or alternatively, the processing system 102 can filter and/or adjust for nonuniform read counts or read depths across the DNA sample set 206. The processing system 102 can remove sample data having the sample read depth 214 below a depth requirement/threshold as described above. The processing system 102 can also adjust for the nonuniformity by calculating and applying the scale factor to the read counts as described above.

At block 818, the computing system 100 can develop and train the ML model 104 using the refined phrases and the refined data samples. For example, the processing system 102 can count and analyze the various somatic mutations, compute correlations between the mutations and cancers, and the like as described above. Using the results, the processing system 102 can select a set of features that include phrases having sufficient correlations to one or more types of cancers. The processing system 102 can design and train the ML model 104 using the selected features (e.g., correlative phrases representative of cancer-causing somatic mutations).

In developing and training the ML model 104, the processing system 102 can further refine the intermediate processing results. For example, at block 820, the processing system 102 can correct for comparison noises, such as by using/implementing the comparison correction filter 258 (FIG. 2). The processing system 102 can correct for the comparison noises using the p-value criteria as described above. Also, at block 822, the processing system 102 can refine the intermediate results per the fractional features. The processing system 102 can use the fraction filter 260 (FIG. 2) in classifying or distinguishing between somatic and non-somatic mutations.

The processing system 102 can develop/train the ML model 104 such that the model is configured to compute a cancer signature (e.g., a score or signal) based on analyzing text-based patient DNA data according to represented somatic indel mutations in patient DNA. The processing system 102 can develop/train the ML model 104 based on computing correlations between mutations (as represented by the derived phrases) and onset/existence of one or more types of cancers as represented by the DNA sample set 206. Using the correlations, the ML model 104 can be configured to compute the cancer signature that represents (1) a likelihood that a corresponding patient has developed the one or more types of cancer, (2) a likelihood that the patient will develop the one or more types of cancer within a given duration, and/or (3) a development status at least leading up to onset of one or more types of cancer.

Figures 9A, 9B:
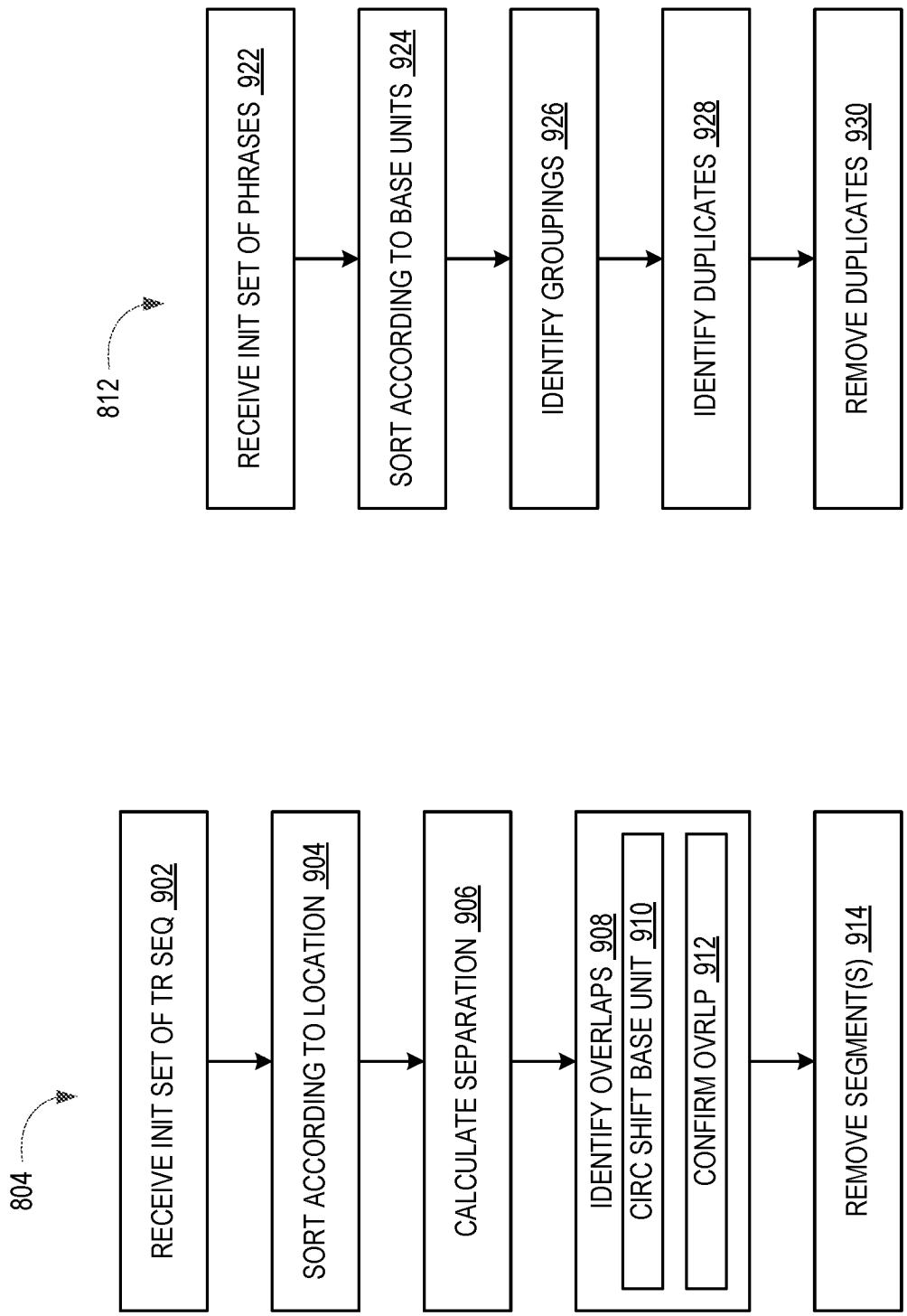
FIGS. 9A-9D are flow charts illustrating example detailed aspects of the method of FIG. 8 in accordance with one or more implementations of the present technology.

Additionally, FIGS. 9A-9D are flow charts illustrating example detailed aspects of the method 800 of FIG. 8 in accordance with one or more implementations of the present technology. FIG. 9A illustrates an example implementation for refining the identifiable text segments (block 804).

At block 902, the computing system 100 can receive an initial set of TR sequences. As described above, the processing system 102 can receive the initial set of TR sequences (e.g., the initial/unrefined instance of the unique segments 360) based on analyzing the human genome and/or accessing externally generated results. The initial set of TR sequences can include location identifiers (e.g., the sequence location 614) that represents a position of the corresponding TR sequence within the overall genome. In some implementations, the initial set of TR sequences can be identified within the genome TR reference catalogue 230.

At block 904, the computing system 100 can sort the initial set of TR sequences according to corresponding location identifiers. For example, the processing system 102 can reorder the TR sequences within a storage mechanism (e.g., array, structure, data table, spreadsheet, etc.) according to their corresponding positions from one end of the human genome to the opposite end.

At block 906, the computing system 100 can calculate separation between location identifiers for adjacently ordered TR sequences. In some implementations, the processing system 102 can calculate a difference or a separation between the location identifiers of TR sequences (e.g., first and second segments) that are adjacently listed in the sorted set of TR sequences.

At block 908, the computing system 100 can identify overlaps. For example, the processing system 102 can identify the overlaps 352 as the TR sequences that are (1) adjacently occurring along the genome and/or adjacently listed in the sorted set and (2) separated by a difference that is less than the base unit length 424.

Additionally or alternatively, the computing system 100 can identify overlaps or verify overlaps based on analyzing the repeated base units 356 of the adjacently ordered TR sequences. At block 910, the computing system 100 can circularly shift the base units (e.g., the repeated base units 356) of adjacently ordered/listed TR sequences. For example, the processing system 102 can circularly shift the repeated base unit 356 of the first segment by the separation/difference in the location identifiers relative to the second segment. Using the example illustrated in FIG. 3B, the processing system 102 can circularly shift the repeated base unit 356 of 'ATC' associated with location 4 by 1 character, which is the difference between locations 4 and 5 of adjacently listed base units. The circularly shifted result of the base unit at location 4 can be 'TCA.'

At block 912, the computing system 100 can confirm overlaps based on comparing the TR sequences. The computing system 100 can identify the overlaps 352 or confirm that adjacently listed base units are the overlaps 352 when the circularly shifted result of a first segment matches a repeated base unit of the second segment. Referring back to the example illustrated in FIG. 3B, the processing system 102 can determine that the TR sequences at locations 4 and 5 are overlaps since the circularly shifted result of the TR sequence at location 4 ('TCA') matches the base unit at location 5. The processing system 102 can identify overlap groupings (e.g., locations 310a, 310b, 310c, and 310d), such as for locations 4-6 overlap each other.

At block 914, the computing system 100 can remove one or more segments from the overlapping group of TR sequences. In some implementations, the processing system 102 can remove one or more segments and retain one or more segments according to a predetermined pattern. For example, the processing system 102 can retain, for each grouping including three or more segments, one segment in a middle portion of the grouping of overlaps.

FIG. 9B illustrates an example implementation for refining the generated phrases (block 812). At block 922, the computing system 100 can receive an initial set of phrases (e.g., the expected phrases 410 and/or the derived phrases 510). In some implementations, the initial set of phrases can correspond to an initial or unrefined instance of the genome TR reference catalogue 230. The processing system 102 can generate the initial set of phrases as described above. Alternatively, the processing system 102 can access the initial set of phrases can access the initial set of phrases previously generated by the computing system 100 or generated by an external system.

In some implementations, the initial set of phrases can include the repeated base unit 356 and the segment length 420 for each phrase. The repeated base unit 356 can represent a text pattern that is repeated for the corresponding TR sequence, and the segment length 420 can correspond to a total number of characters for the corresponding TR sequence.

At block 924, the computing system 100 can sort the phrases according to the base units (e.g., the repeated base units 356). For example, the processing system 102 can sort the phrases according to the corresponding repeated base units 356. The processing system 102 can reorder the arrangement of the phrase in the initial set according to the segment length 420 and/or one or more alphabetic sorting rules.

At block 926, the computing system 100 can identify groupings of phrases according to base units. For example, the processing system 102 can identify phrase groupings based on the sorted phrases. The processing system 102 can identify the groupings as adjacently arranged phrases having matching instances of the repeated base units 356 and the segment length 420.

At block 928, the computing system 100 can identify duplicates based on the groupings. For example, the processing system 102 can identify the groupings as matching character sequences in the duplicates. In other words, the processing system 102 can compare the flanking characters of the phrases within the groupings. The processing system 102 can identify the duplicates as the phrases having matching character sequences/patterns.

At block 930, the computing system 100 can remove the duplicates. For example, the processing system 102 can remove the duplicates to generate the refined set of phrases that include the expected phrases 410 and/or the derived phrases 510 for developing the ML model 104.

In other implementations, the processing system 102 can generate the phrases without removing the overlaps. The processing system 102 can remove the overlaps and duplicates from the initial set of phrases.

Figures 9C, 9D:
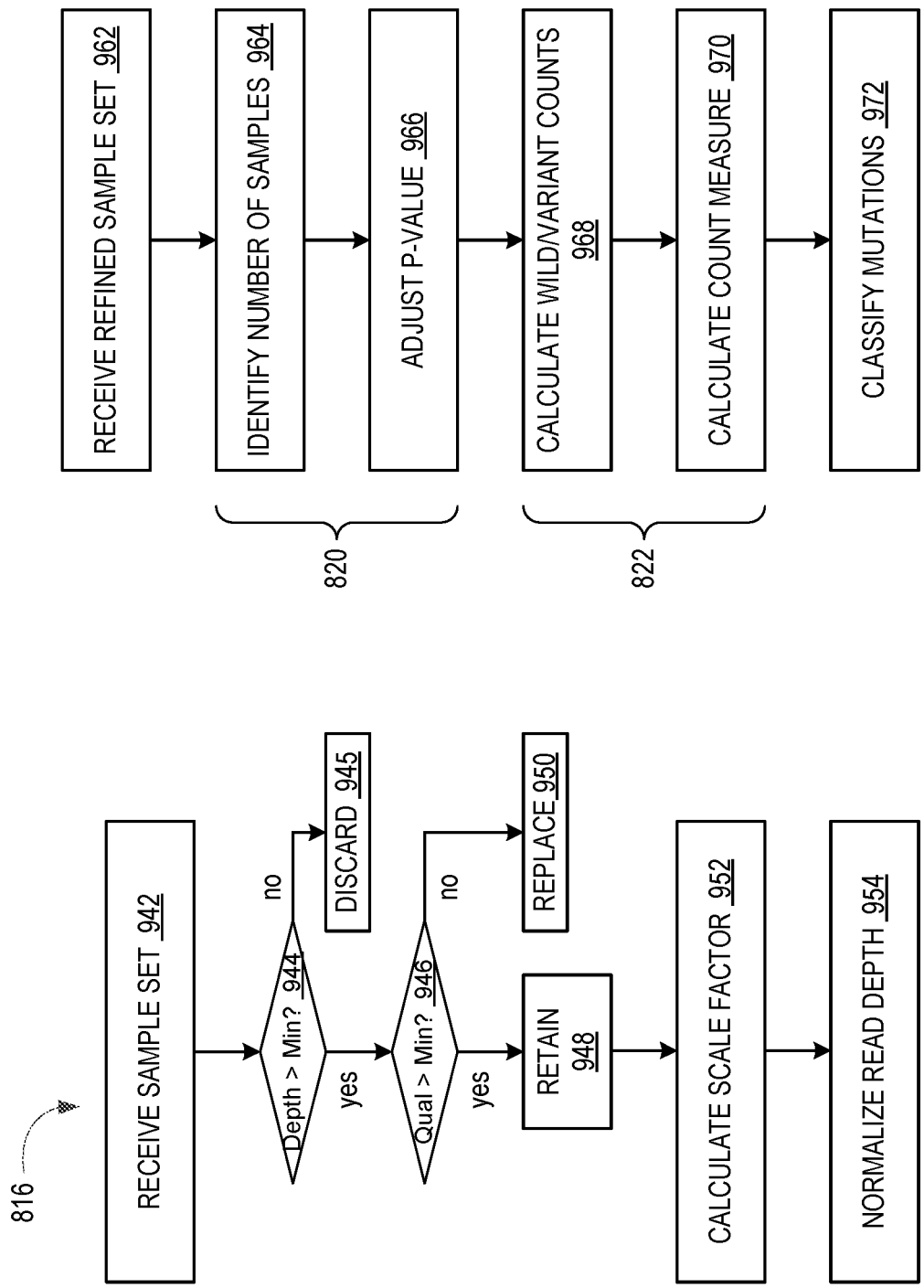

FIG. 9C illustrates an example implementation for refining the data samples (block 816). At block 942, the computing system 100 can receive the sample set (e.g., the DNA sample set 206) for developing/training the ML model 104. For example, the processing system 102 can receive the DNA sample set 206 that includes text strings representative of DNA data. The represented DNA data can be from (1) patients confirmed to have one or more types of cancer (e.g., the cancer-specific data 212), (2) patients confirmed to be without cancer (e.g., the cancer-free data 210), and/or (3) samples collected from locations/regions separate from the cancer-effected region, such as leukocyte or white blood cells, in patients with and/or without cancer. The DNA sample set 206 can have data corresponding to different sample read depths 214.

At decision block 944, the computing system 100 can determine whether the depth measures (e.g., the sample read depths 214) for the sample set satisfies (e.g., greater than a minimum) threshold requirement. The computing system 100 can discard the data with insufficient read depth as illustrated at block 945.

For the data corresponding to satisfactory depth measures, the computing system 100 can determine whether the quality measures for the sample set satisfies (e.g., greater than a minimum) threshold requirement, such as illustrated at decision block 946. At block 948, the computing system 100 can retain the sample data satisfying the minimum depth requirement and/or the minimum quality requirement. Otherwise, the computing system 100 can replace the characters of the sample data corresponding to insufficient quality measure to a predetermined character (e.g., 'N') as illustrated at block 950. Accordingly, the computing system 100 can retain a refined set of the sample DNA data (e.g., corresponding text strings) satisfying the minimum read depth/quality requirement(s).

In some implementations, the computing system 100 can further adjust for differences in read depths across different samples and/or groupings thereof. At block 952, the computing system 100 can calculate one or more scale factors configured for use in adjusting for the different read depths. For example, the processing system 102 can calculate a cancer-free scale factor for the cancer-free data 210 and/or a cancer-specific scale factor for the cancer-specific data 212 based on a normalization parameter (e.g., a predetermined normalization factor 'a'). In some implementations, the processing system 102 can calculate the cancer-free scale factor as a divided by a number of healthy data reads (e.g., the sample read depth 214 for the cancer-free data 210). Similarly, the processing system 102 can calculate the cancer-specific scale factor as α divided by a number of tumorous data reads (e.g., the sample read depth 214 for the cancer-specific data 212).

At block 954, the computing system 100 can normalize the different read depths. In some implementations, the processing system 102 can use the sample set as refined according to operations illustrated in blocks 942-950. Otherwise, the processing system 102 can normalize the initial sample set. The processing system 102 can normalize the different read depths using the corresponding scale factors. For example, the processing system 102 can normalize the count for the wild type matches in the cancer-free data 210 by multiplying the count by the cancer-free scale factor. Similarly, the processing system 102 can normalize the count for the indel mutations in the cancer-free data 210 by multiplying the count by the cancer-free scale factor. Also, the processing system 102 can normalize the counts for the wild type matches and the indel mutations in the cancer-specific data 212 by multiplying the raw counts by the cancer-specific scale factor.

FIG. 9D illustrates an example implementation for refining intermediate data results during development/training for the ML model 104 (block 818). At block 962, the computing system 100 can receive the refined instance of the DNA sample set 206. The refined set can include text strings representative of DNA data associated with at least (1) patients confirmed to have one or more types of cancer (e.g., the cancer-specific data 212) and (2) patients confirmed to be without cancer (e.g., the cancer-free data 210).

The computing system 100 can analyze the received DNA sample set 206 using the refined set of phrases. For example, the processing system 102 can compute the correlations between various mutations and the existence of one or more types of cancer as reflected in the DNA sample set 206. In some implementations, the processing system 102 can identify wild type mutations, somatic mutations, indel mutations, and the like. The processing system 102 can compute the correlation based on specific somatic indel mutations that occur at least a minimum number of times in the cancer-specific data 212 and occur less than a required number of time in the cancer-free data 210.

In developing the ML model, the processing system 102 can correct for comparison noises as discussed above for block 820. As an illustrative example, the processing system 102 can correct for the number of noises by reducing false positive results from multiple comparisons. In some implementations, the correction can be implemented by identifying a number of samples as illustrated in block 964. For example, during binomial processing to compare cancer-free and tumor patters, the processing system 102 can identify the number of TR patterns involved in the binomial processing portion. At block 966, the processing system 102 can adjust or divide the statistically relevant results, such as the p-value criteria (e.g., an intermediate processing result used to determine whether the observed difference is statistically significant), by the identified number of TR patterns. For example, the processing system can perform a Bonferroni correction using the number of TR patterns and the p-value criteria.

Further during developing the ML model, the processing system 102 can refine per fractions or physiological/biological patterns as discussed above for block 822. As an illustrative example, the processing system 102 can filter for relatively low mutant counts. To filter, the processing system 102 can calculate various counts, such as the wild type count (e.g., a number of occurrences of one or more genes found in natural non-mutated form) and the mutant variant count (e.g., a number of occurrences of a target derived phrase), from the DNA sample set 206 as illustrated at block 968. At block 970, the processing system 102 can calculate a representative count measure for the mutant variant based on the wild type count and the mutant variant count. For example, the processing system 102 can calculate the representative measure based on dividing the mutant variant count by the sum of the wild type count and the mutant variant count.

At block 972, the processing system 102 can classify one or more mutations for further analysis (e.g., correlation computations) in developing the ML model. In some implementations, the processing system 102 can use the adjusted p-value to classify the mutations. For example, the processing system 102 can classify mutations or corresponding derived phrases as non-somatic using the adjusted p-value as a classification threshold. Additionally or alternatively, the processing system 102 can use the representative measure (e.g., an allelic fraction) for the somatic classification. For example, the processing system 102 can identify non-somatic mutations with low mutant counts when the representative measure is less than a predetermined threshold. The processing system 102 can remove the non-somatic mutations from subsequent processing, such as the correlation computation.

The processing system 102 using the refinement mechanism 115 to refine the data and/or intermediate results provide reduced resource consumption. For example, by removing the overlaps in the unique segments 360, the processing system 102 can reduced the various phrases at an exponential rate. Also, by removing the duplicate phrases, the processing system 102 can similarly reduce the corresponding processing resources. Moreover, the processing system 102 can use the refinement mechanism 115 to increase the accuracy of the ML model 104 to generate the cancer signature. The processing system 102 can increase the accuracy by removing the overlaps and duplicates that may attribute inaccurate weight or effect to overlapped or duplicated mutations. Also, the processing system 102 can increase the accuracy by accounting for the read depth differences and accurately identifying somatic and non-somatic mutations.

Computing System

Figure 10:
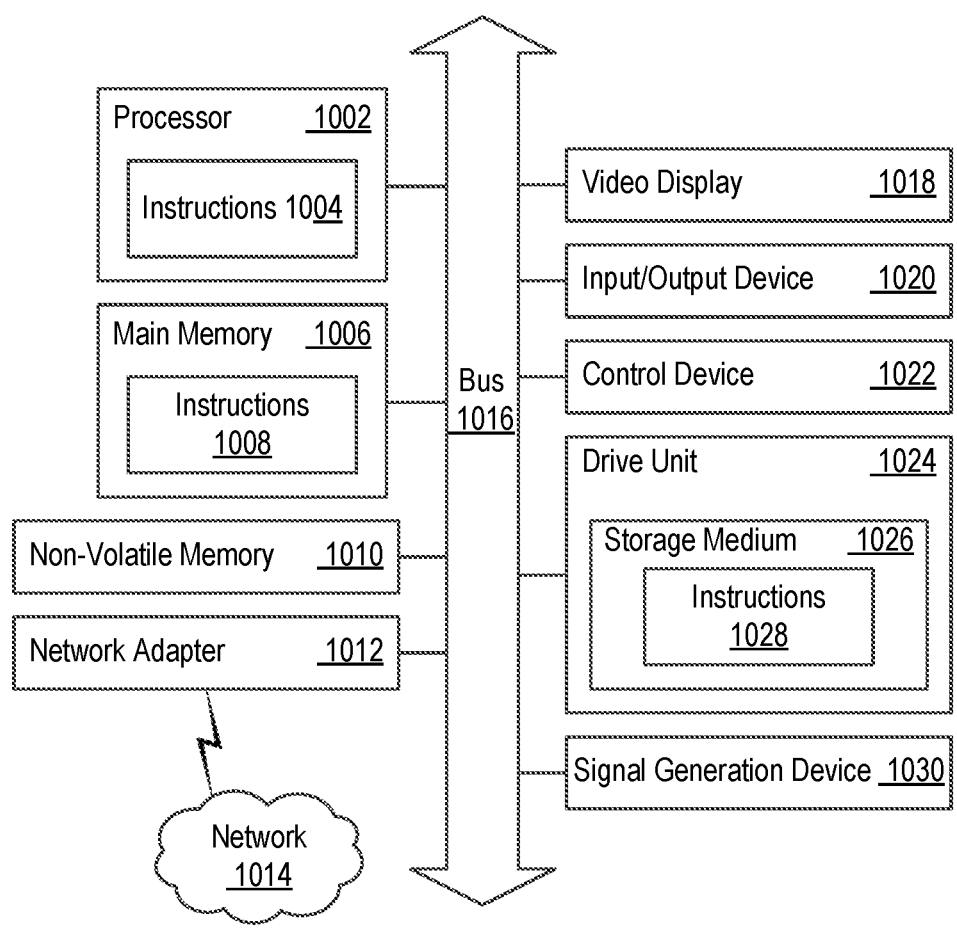
FIG. 10 is a block diagram illustrating an example of a system in accordance with one or more implementations of the present technology.

FIG. 10 is a block diagram illustrating an example of a system 1000 (e.g., the computing system 100 or a portion thereof, such as the processing system 102) in accordance with one or more implementations of the present technology. For example, some components of the system 1000 may be hosted on a computing device that includes a mutation analysis mechanism and a refinement mechanism.

The system 1000 may include a processor 1002, main memory 1006, non-volatile memory 1010, network adapter 1012, video display 1018, input/output device 1020, control device 1022 (e.g., a keyboard or pointing device), drive unit 1024 including a storage medium 1026, and signal generation device 1030 that are communicatively connected to a bus 1016. The bus 1016 is illustrated as an abstraction that represents one or more physical buses or point-to-point connections that are connected by appropriate bridges, adapters, or controllers. The bus 1016, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), inter-integrated circuit ($I^2C$) bus, or an Institute of Electrical and Electronics Engineers (IEEE) standard 1394 bus (also referred to as "Firewire").

While the main memory 1006, non-volatile memory 1010, and storage medium 1026 are shown to be a single medium, the terms "machine-readable medium" and "storage medium" should be taken to include a single medium or multiple media (e.g., a centralized/distributed database and/or associated caches and servers) that store one or more sets of instructions 1028. The terms "machine-readable medium" and "storage medium" shall also be taken to include any medium that is capable of storing, encoding, or carrying a set of instructions for execution by the system 1000.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1004, 1008, 1028) set at various times in various memory and storage devices in a computing device. When read and executed by the processors 1002, the instruction(s) cause the system 1000 to perform operations to execute elements involving the various aspects of the present disclosure.

Further examples of machine- and computer-readable media include recordable-type media, such as volatile memory devices and non-volatile memory devices 1010, removable disks, hard disk drives, and optical disks (e.g., Compact Disk Read-Only Memory (CD-ROMS) and Digital Versatile Disks (DVDs)), and transmission-type media, such as digital and analog communication links.

The network adapter 1012 enables the system 1000 to mediate data in a network 1014 with an entity that is external to the system 1000 (e.g., between the processing system 102 can the sourcing device 152) through any communication protocol supported by the system 1000 and the external entity. The network adapter 1012 can include a network adaptor card, a wireless network interface card, a router, an access point, a wireless router, a switch, a multilayer switch, a protocol converter, a gateway, a bridge, bridge router, a hub, a digital media receiver, a repeater, or any combination thereof.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A non-transitory medium with instructions stored thereon that, when executed by a processor of a computing device, cause the computing device to perform operations comprising:
generating text phrases that represent different DNA sequences,
wherein the text phrases include—
expected phrases corresponding to multiple locations in an overall genome, wherein phrases corresponding to each location include different combinations of flanking texts adjacent to a text segment that represents a tandem repeat (TR) sequence associated with the corresponding location, and
derived phrases representative of sampled mutations in the TR sequence, and
wherein generating the text phrases includes refining an initial set of segments and/or phrases based on removing overlaps and/or duplicates therein to generate the text phrases,
wherein the initial set includes:
segments representative of TR sequences that each include N number of adjacently repeated base units, wherein the repeated base units have a base unit length uniform across the segments, and
a location for each of the segments, wherein the location represents a position of the corresponding TR sequence within the overall genome, and
wherein refining the initial set includes—
sorting the initial set according to locations;
based on the sorted result, calculating a separation in location values between adjacently occurring segments;
identifying the adjacently occurring segments as the overlaps when the separation in location values is less than the base unit length;
removing one or more segments in the overlaps according to a predetermined pattern; and
generating a refined set of segments and/or phrases based on removing the overlaps from the initial set, wherein the overlaps represent TR sequences that are within the base unit length from each other; and
developing a machine learning (ML) model based on using a subset of the text phrases as features, wherein the ML model is trained and configured to compute a cancer signature based on analyzing text-based patient DNA data according to representations therein of mutations in patient DNA, the cancer signature representing (1) a likelihood that a corresponding patient has developed one or more types of cancer, (2) a likelihood that the patient will develop the one or more types of cancer within a given duration, (3) a development status at least leading up to onset of the one or more types of cancer, (4) monitoring a progression or a treatment response of the one or more types of cancer, or a combination thereof.

2. The non-transitory medium of claim 1, wherein removing one or more segments includes retaining one segment in a middle portion of the overlaps when the overlaps include three or more segments.

3. The non-transitory medium of claim 1, wherein refining the initial set further includes:
based on the sorted result, calculating a separation in location values between a first segment and a second segment that are adjacent to each other;
circularly shifting a repeated base unit of the first segment by the separation in location values; and
identifying or confirming that the first and second segments are overlaps when the circularly shifted result matches a repeated base unit of the second segment.

4. The non-transitory medium of claim 1, wherein:
the initial set includes phrases corresponding to different locations in the overall genome, wherein each of the phrases has a length k and includes a location-specific TR-based segment or an indel derivation thereof adjacent to a corresponding set of flanking texts; and
refining the initial set includes generating a refined set of phrases based on removing duplicates from the initial set of phrases, wherein the duplicates represent matching character sequences that are associated with differing locations.

5. A non-transitory medium with instructions stored thereon that, when executed by a processor of a computing device, cause the computing device to perform operations comprising:
generating text phrases that represent different DNA sequences,
wherein the text phrases include—
expected phrases corresponding to multiple locations in an overall genome, wherein phrases corresponding to each location include different combinations of flanking texts adjacent to a text segment that represents a tandem repeat (TR) sequence associated with the corresponding location, and
derived phrases representative of sampled mutations in the TR sequence,
wherein generating the text phrases includes refining an initial set of segments and/or phrases based on removing overlaps and/or duplicates therein to generate the text phrases,
wherein the initial set includes:
phrases corresponding to different locations in the overall sequence, wherein each of the phrases has a length k and includes a location-specific TR-based segment or an indel derivation thereof adjacent to a corresponding set of flanking texts, and
a repeated base unit and a segment length for each phrase, wherein the repeated base unit represents a text pattern that is repeated for the corresponding TR sequence and the segment length corresponds to a total number of characters for the corresponding TR sequence, and
wherein refining the initial set includes—
sorting the initial set according to the repeated base unit and the segment length;
based on the sorted result, identifying phrase groupings that each include adjacently arranged phrases with matching repeated base unit and matching segment length;
identifying duplicates based on the phrase groupings, wherein the duplicates include matching character patterns; and
removing the duplicates to generate the refined set of phrases that include the expected phrases and/or the derived phrases used to develop the ML model; and
generating a refined set of phrases based on removing duplicates from the initial set, wherein the duplicates represent matching character sequences that are associated with differing locations; and
developing a machine learning (ML) model based on using a subset of the text phrases as features, wherein the ML model is trained and configured to compute a cancer signature based on analyzing text-based patient DNA data according to representations therein of mutations in patient DNA, the cancer signature representing (1) a likelihood that a corresponding patient has developed one or more types of cancer, (2) a likelihood that the patient will develop the one or more types of cancer within a given duration, (3) a development status at least leading up to onset of the one or more types of cancer, (4) monitoring a progression or a treatment response of the one or more types of cancer, or a combination thereof.

6. The non-transitory medium of claim 4, wherein the initial set of phrases is generated based on (1) including the flanking text and/or (2) identifying indel derivations of a refined set of text segments resulting from removing overlaps in an initial set of text segments representative of location-specific TR sequences.

7. The non-transitory medium of claim 4, wherein:
the initial set of phrases is generated based on an initial set of segments that include overlaps; and
refining the initial set includes—
removing overlapping phrases corresponding to the overlaps in the initial set of segments; and
generating the refined set of phrases after removing the overlapping phrases.

8. The non-transitory medium of claim 1, wherein developing the ML model includes:
receiving a DNA sample set that includes text strings representative of DNA data associated with (1) patients confirmed to have one or more types of cancer and (2) patients confirmed to be without cancer, wherein the text strings are associated with different sample read depths;
retaining a refined set of sample text strings having the sample read depths satisfying a minimum read depth threshold; and
developing the ML model based on selecting the features and/or training using the refined set of DNA sample set.

9. A non-transitory medium with instructions stored thereon that, when executed by a processor of a computing device, cause the computing device to perform operations comprising:

generating text phrases that represent different DNA sequences,
wherein the text phrases include—
expected phrases corresponding to multiple locations in an overall genome, wherein phrases corresponding to each location include different combinations of flanking texts adjacent to a text segment that represents a tandem repeat (TR) sequence associated with the corresponding location, and
derived phrases representative of sampled mutations in the TR sequence, and
wherein generating the text phrases includes refining an initial set of segments and/or phrases based on removing overlaps and/or duplicates therein to generate the text phrases; and
developing a machine learning (ML) model based on using a subset of the text phrases as features, wherein the ML model is trained and configured to compute a cancer signature based on analyzing text-based patient DNA data according to representations therein of mutations in patient DNA, the cancer signature representing (1) a likelihood that a corresponding patient has developed one or more types of cancer, (2) a likelihood that the patient will develop the one or more types of cancer within a given duration, (3) a development status at least leading up to onset of the one or more types of cancer, (4) monitoring a progression or a treatment response of the one or more types of cancer, or a combination thereof,
wherein developing the ML model includes:
receiving a DNA sample set that includes text strings representative of DNA data associated with (1) patients confirmed to have one or more types of cancer and (2) patients confirmed to be without cancer, wherein the text strings are associated with different sample read depths;
retaining a refined set of sample text strings having the sample read depths satisfying a minimum read depth threshold;
developing the ML model based on selecting the features and/or training using the refined set of DNA sample set;
calculating at least a cancer-free scale factor and a cancer-specific scale factor based on a normalization parameter; and
using the refined set of retained sample text strings, normalizing the different sample read depths for the cancer-confirmed text strings and the cancer-free text strings using the cancer-specific scale factor and the cancer-free scale factor, respectively.

10. The non-transitory medium of claim 1, wherein developing the ML model includes:
receiving a DNA sample set that includes text strings representative of DNA data associated with (1) patients confirmed to have one or more types of cancer and (2) patients confirmed to be without cancer, wherein the text strings are associated with sample quality scores;
retaining a refined set of sample text strings having the sample quality scores satisfying a minimum quality threshold; and
developing the ML model based on selecting the features and/or training using the refined set of DNA sample set.

11. A non-transitory medium with instructions stored thereon that, when executed by a processor of a computing device, cause the computing device to perform operations comprising:
   generating text phrases that represent different DNA sequences,
      wherein the text phrases include—
         expected phrases corresponding to multiple locations in an overall genome, wherein phrases corresponding to each location include different combinations of flanking texts adjacent to a text segment that represents a tandem repeat (TR) sequence associated with the corresponding location, and
         derived phrases representative of sampled mutations in the TR sequence, and
      wherein generating the text phrases includes refining an initial set of segments and/or phrases based on removing overlaps and/or duplicates therein to generate the text phrases; and
   developing a machine learning (ML) model based on using a subset of the text phrases as features, wherein the ML model is trained and configured to compute a cancer signature based on analyzing text-based patient DNA data according to representations therein of mutations in patient DNA, the cancer signature representing (1) a likelihood that a corresponding patient has developed one or more types of cancer, (2) a likelihood that the patient will develop the one or more types of cancer within a given duration, (3) a development status at least leading up to onset of the one or more types of cancer, (4) monitoring a progression or a treatment response of the one or more types of cancer, or a combination thereof,
      wherein developing the ML model includes reducing false positives resulting from multiple comparisons by (1) adjusting a p-value criteria by a number of the TR sequences used in the multiple comparisons and (2) identifying somatic mutations based on the adjusted p-value criteria, wherein the somatic mutations are retained for considering correlations to the one or more types of cancer.

12. A non-transitory medium with instructions stored thereon that, when executed by a processor of a computing device, cause the computing device to perform operations comprising: generating text phrases that represent different DNA sequences, wherein the text phrases include—
   expected phrases corresponding to multiple locations in an overall genome, wherein phrases corresponding to each location include different combinations of flanking texts adjacent to a text segment that represents a tandem repeat (TR) sequence associated with the corresponding location, and derived phrases representative of sampled mutations in the TR sequence, and wherein generating the text phrases includes refining an initial set of segments and/or phrases based on removing overlaps and/or duplicates therein to generate the text phrases; and developing a machine learning (ML) model based on using a subset of the text phrases as features, wherein the ML model is trained and configured to compute a cancer signature based on analyzing text-based patient DNA data according to representations therein of mutations in patient DNA, the cancer signature representing (1) a likelihood that a corresponding patient has developed one or more types of cancer, (2) a likelihood that the patient will develop the one or more types of cancer within a given duration, (3) a development status at least leading up to onset of the one or more types of cancer, (4) monitoring a progression or a treatment response of the one or more types of cancer, or a combination thereof, wherein developing the ML model includes:
receiving a DNA sample set that includes text strings representative of DNA data associated with (1) patients confirmed to have one or more types of cancer and (2) patients confirmed to be without cancer;
calculating a wild type count based on analyzing the DNA sample set, wherein the wild type count represents a number of occurrences of one or more genes found in natural non-mutated form within the DNA sample set;
calculating a variant count based on analyzing the DNA sample set, wherein the variant count represents a number of occurrences of a target derived phrase within the DNA sample set;
calculating a variant count measure for the target derived phrase based on the wild type count and the variant count; and
classifying a target mutation represented by the target derived phrase as non-somatic when the variant count measure is less than a minimum threshold.

* * * * *

UNITED STATES PATENT AND TRADEMARK OFFICE
CERTIFICATE OF CORRECTION

PATENT NO.        : 11,935,627 B2
APPLICATION NO.   : 18/146901
DATED             : March 19, 2024
INVENTOR(S)       : Cheuk Ying Tang et al.

Page 1 of 1

It is certified that error appears in the above-identified patent and that said Letters Patent is hereby corrected as shown below:

On the Title Page

At (73), delete "Mujin, Inc., Tokyo (JP)" and insert -- AIONCO, Inc., Menlo Park, CA (US) --.

In the Specification

In Column 15, Line 36, delete "Trackinq" and insert -- Tracking --.

Signed and Sealed this
Fifth Day of August, 2025

Coke Morgan Stewart
*Acting Director of the United States Patent and Trademark Office*